(12) United States Patent
Bikson et al.

(10) Patent No.: US 8,965,514 B2
(45) Date of Patent: Feb. 24, 2015

(54) TRANSCRANIAL STIMULATION

(75) Inventors: Marom Bikson, Brooklyn, NY (US);
Abhishek Datta, New York, NY (US);
Varun Bansal, Maspeth, NY (US);
Lucas C. Parra, Brooklyn, NY (US);
Xiang Zhou, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 370 days.

(21) Appl. No.: 13/264,139

(22) PCT Filed: Apr. 13, 2010

(86) PCT No.: PCT/US2010/030945

§ 371 (c)(1),
(2), (4) Date: May 4, 2012

(87) PCT Pub. No.: WO2010/120824

PCT Pub. Date: Oct. 21, 2010

(65) Prior Publication Data

US 2012/0209346 A1    Aug. 16, 2012

Related U.S. Application Data

(60) Provisional application No. 61/168,861, filed on Apr. 13, 2009, provisional application No. 61/310,123, filed on Mar. 3, 2010.

(51) Int. Cl.
*A61N 1/00* (2006.01)
*A61N 1/20* (2006.01)
*A61N 1/08* (2006.01)
*A61N 1/36* (2006.01)
*A61N 1/04* (2006.01)

(52) U.S. Cl.
CPC .. *A61N 1/20* (2013.01); *A61N 1/08* (2013.01);
*A61N 1/36025* (2013.01); *A61N 1/0408* (2013.01); *A61N 1/0476* (2013.01)
USPC ............... 607/45; 607/46; 607/62; 607/64

(58) Field of Classification Search
USPC ................. 607/1–3, 139, 62–64, 148, 45, 46
See application file for complete search history.

(56) References Cited

U.S. PATENT DOCUMENTS 4,554,928 A    11/1985    Webster, Jr.
4,907,601 A *  3/1990     Frick .............................. 607/72

(Continued)

OTHER PUBLICATIONS

An International Search Report mailed Nov. 29, 2010, which issued in corresponding International Application No. PCT/US2010/030945.

*Primary Examiner* — Michael Kahelin
*Assistant Examiner* — Mallika D Fairchild
(74) *Attorney, Agent, or Firm* — Hoffman & Baron, LLP

(57) ABSTRACT

A method includes coupling electrodes to a patient's head and identifying whether any of the electrodes form a functional set, such that a desired therapeutic effect is achieved when the two or more electrodes deliver a total amount of current to the patient regardless of what portion of the total amount of current each respective electrode carries. One or more constant current sources are provided, each having a supply and return terminal, which supply and return equal amounts of current at any given time. The constant current source(s) are coupled to the electrodes in such a manner that each supply terminal and each return terminal is coupled to no more than the electrodes of a single one of the functional sets, if any, or to a single one of the electrodes not included in one of the functional sets.

24 Claims, 19 Drawing Sheets

(56) References Cited

U.S. PATENT DOCUMENTS

| | | |
|---|---|---|
| 5,540,736 A | 7/1996 | Haimovich et al. |
| 2003/0187490 A1 | 10/2003 | Gliner |
| 2004/0158298 A1 | 8/2004 | Gliner et al. |
| 2006/0015153 A1 | 1/2006 | Gliner et al. |
| 2006/0259094 A1 * | 11/2006 | Naisberg et al. ............... 607/45 |
| 2008/0208287 A1 | 8/2008 | Palermo et al. |

* cited by examiner

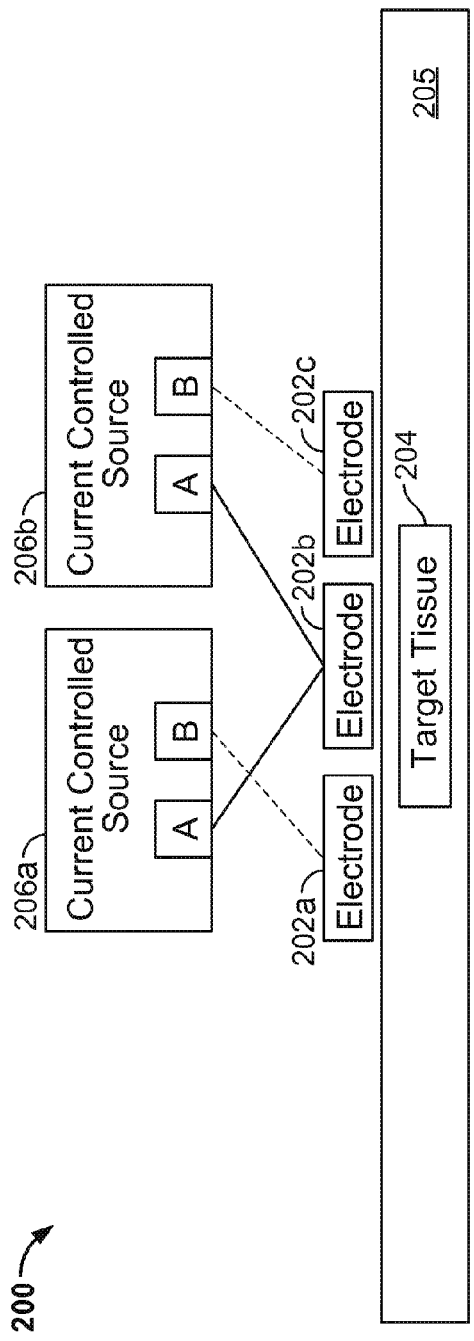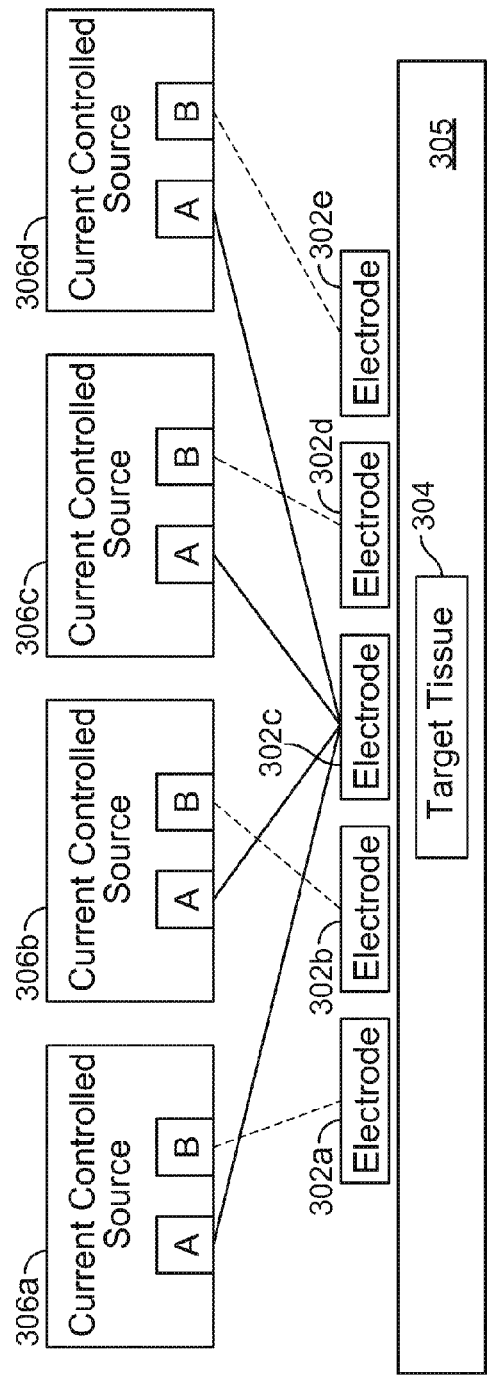

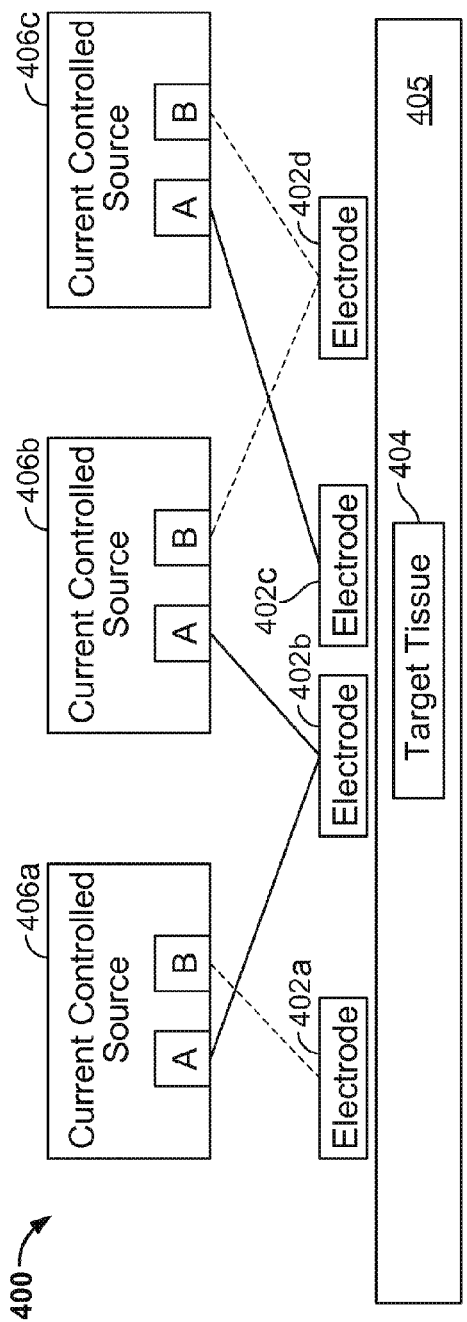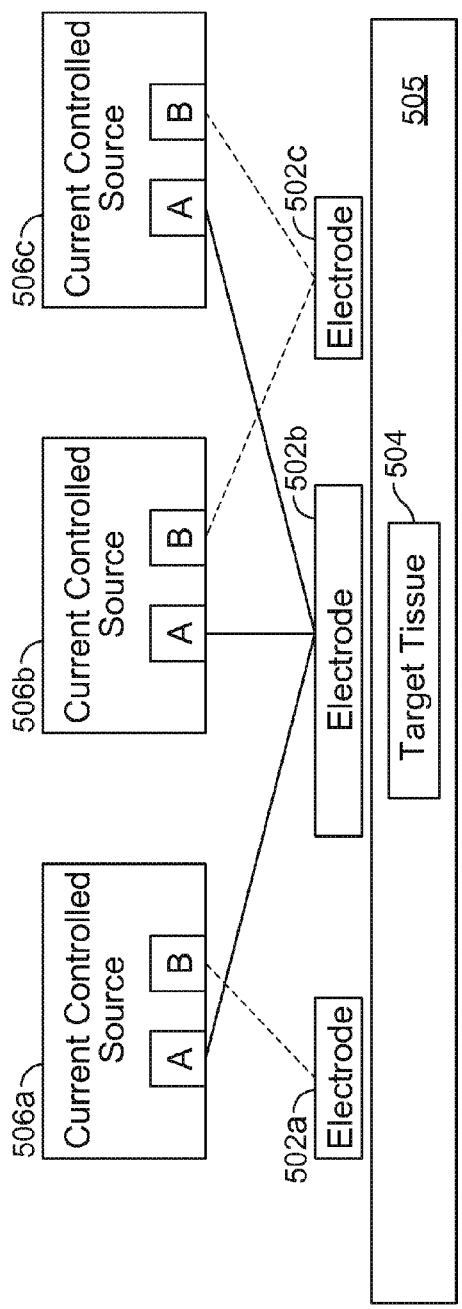

Sq 0.4mA Bipolar
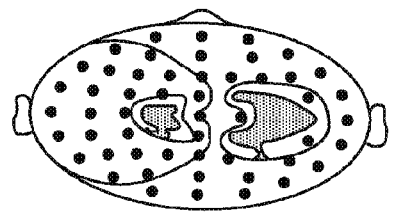
1Hz 0.4mA Bipolar
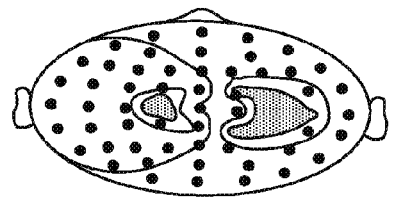
10Hz 0.4mA Bipolar
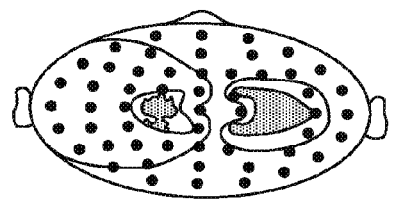
100Hz 0.4mA Bipolar
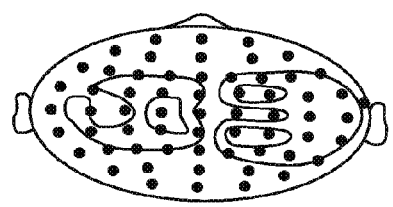
10Hz 0.4mA 4 by 1
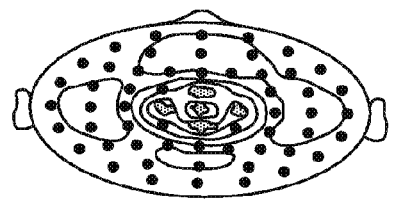
FIG. 16

Cortical Induced Electric Field
(Tangential Component)
Passive Control (Good Contact)
Passive Control (Bad Contact)
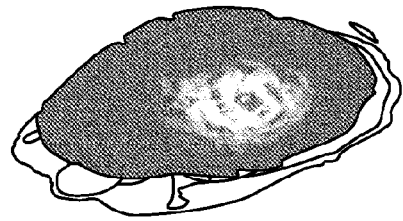
0.110 V/m
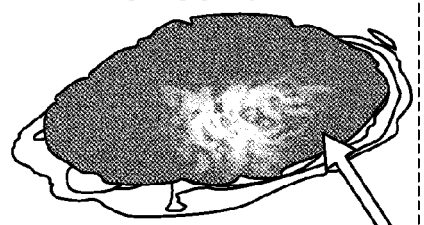
0.130 V/m
Bad Contact
Active Control (Good Contact)
Active Control (Bad Contact)
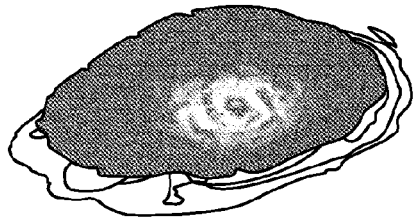
0.110 V/m
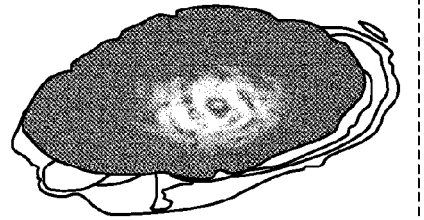
0.110 V/m
FIG. 22

TRANSCRANIAL STIMULATION

CROSS REFERENCE TO PRIOR APPLICATIONS

This is a U.S. National Phase application under 35 U.S.C. §371 of International Patent Application No. PCT/US2010/030945, filed Apr. 13, 2010, and claims the priority of U.S. Provisional Patent Application No. 61/310,123, filed Mar. 3, 2010 and U.S. Provisional Patent Application No. 61/168,861, filed Apr. 13, 2009 all of which are incorporated by reference herein. The International Application published in English on Oct. 21, 2010 as WO 2010/120824 under PCT Article 21(2).

CROSS-REFERENCE TO RELATED APPLICATION(S)

This application claims the benefits of and priority to U.S. Provisional Patent Application Ser. No. 61/168,861, filed Apr. 13, 2009 and to U.S. Provisional Patent Application Ser. No. 61/310,123, filed Mar. 3, 2010, the disclosures of which are incorporated herein by reference.

FIELD OF THE INVENTION

The present disclosure relates to transcranial stimulation and, more particularly, relates to systems, devices and techniques to apply transcranial stimulation.

BACKGROUND

Acute or plastic changes in brain function can be safely induced in humans by low-intensity electrical stimulation by delivering current through electrodes on a patient's scalp. Such electrical stimulation is sometime referred to as Neurocranial electrostimulation (NCS). These changes can be potentially used for therapeutic or performance enhancing applications. Currently available devices and techniques tend to be rudimentary, untargeted, inefficient, and/or unsafe. In a typical technique, stimulation is provided through one or more pairs of relatively-large, sponge-like electrodes.

Transcranial electrical stimulation generally refers to short-duration (e.g., 50-500 μs) of supra-threshold pulses (e.g., 100-1200 V). Cranial electrotherapy stimulation (CES) generally utilizes a range of waveforms with peak current levels ranging from 50 μA to 5 mA. Supra-threshold current pulse trains (about 0.9 A) are generally used during electroconvulsive therapy (ECT). DC waveforms ranging from about 260 μA to 2 mA are sometimes used for transcranial direct current stimulation (tDCS).

Transcranial AC stimulation uses AC currents.

SUMMARY OF THE INVENTION

The present disclosure relates to transcranial stimulation and, more particularly, relates to systems, devices and techniques to apply transcranial stimulation.

In one aspect, a method includes coupling two or more electrodes to a patient's head and identifying whether two or more of the electrodes form a functional set, such that a desired therapeutic effect can be achieved when the two or more electrodes deliver a total amount of current to the patient regardless of what portion of the total amount of current each respective electrode in the functional set delivers. The method includes providing one or more constant current sources, each having a supply terminal and a return terminal. The current supplied at the supply terminal at any given time is equal to current returned to the return terminal. The one or more constant current sources are coupled to the electrodes in such a manner that each supply terminal and each return terminal is coupled to no more than the electrodes of a single one of the functional sets, if any, or to a single one of the electrodes not included in one of the functional sets.

In one aspect, a method includes coupling electrodes to a patient's head and identifying (either before, during or after coupling) whether two or more of the electrodes form a functional set. Typically, a functional set of two or more electrodes exists where a desired therapeutic effect can be achieved when the two or more electrodes delivers a total amount of current to the patient regardless of what portion of the total amount of current each respective electrode in the functional set delivers. The method includes providing one or more constant (and typically adjustable) current sources, each having a supply terminal and a return terminal. The current supplied at the supply terminal is equal to current returned to the return terminal. The method includes coupling the one or more constant current sources to the electrodes in such a manner that each supply terminal and each return terminal is coupled to no more than the electrodes of a single one of the functional sets, if any, or to a single one of the electrodes not included in one of the functional sets.

In a typical implementation, the foregoing arrangement provides independent current control to each electrode or functional set of electrodes in the patient.

In some implementations, the method includes coupling more than one of the supply terminals or more than one of the return terminals to the electrodes of a single one of the functional sets, if any, or to a single one of the electrodes, if any, not included in the functional sets.

The method typically includes delivering a substantially constant amount of current to each respective functional set, if any and/or delivering a substantially constant amount of current to each respective electrode, if any, not included in one of the functional sets.

According to certain implementations, the method includes limiting a rate of change associated with the current being delivered to each electrode to no more than approximately 1 milliamp per second. If, for example, the amount of current being supplied to one of the electrodes is being changed (either automatically or manually), the rate of change is limited (either automatically or manually) to not more than 1 milliamp per second.

The plurality of electrodes can includes at least one functional set or can include no functional sets. The plurality of electrodes can includes at least one electrode not included in one of the functional sets or can include no electrodes that are not in a functional set.

Identifying the one or more functional sets typically includes considering one or more of the following factors: physical proximity of same polarity electrodes to one another, electrical resistance between adjacent or closely located same polarity electrodes; and physical arrangement of electrodes having a first polarity relative to electrodes of a second polarity.

A functional set can include one or more of the following: a pair of same polarity electrodes that are of one another less than about 4 centimeters, more preferably less than about 2 centimeter of one another and most preferably touching one another. Similarly, a functional set can include one or more of the following: a pair of same polarity electrodes that have a resistance between them of less than about 1 kohm, less than about 200 ohms, less than about 100 ohms, less than about 10 ohms, less than about 1 ohm or close to zero ohms. Similarly, a functional set can include a same polarity electrode (i.e., an electrode having a first polarity) or a plurality of same polarity electrodes (i.e., electrodes having the first polarity) surrounded by three or more electrodes having an opposite polarity (i.e., a second polarity different than the first polarity). In some instances, two or more electrodes that are physically in contact with one another form a functional set.

According to some embodiments, identifying whether two or more of the electrodes form a functional set includes measuring or estimating a resistance from one electrode to another electrode of the same polarity. In some implementations, identifying whether two or more of the electrodes form a functional set includes identifying one or more electrodes of a first polarity substantially surrounded by four electrodes of a second polarity different than the first.

The method can include delivering current to the patient's body from the supply terminal of a single one of the constant current sources through the four electrodes of the second polarity; and returning current from the patient's body to the return terminal of the single one of the constant current sources through the one or more electrodes of the first polarity.

In certain implementations, the includes delivering current to the patient's body from the supply electrode of a single one of the constant current sources through the one or more electrodes of the first polarity; and returning current from the patient's body to the return terminal of the single one of the constant current sources through the four electrodes of the second polarity. In some implementations, the method includes delivering current to the patient's body from the supply terminals of four constant current sources through the four electrodes of the second polarity, respectively; and returning current from the patient's body to the return terminals of the four constant current sources through the one or more electrodes of the first polarity.

Certain embodiments include delivering current to the patient's body from the supply terminals of four constant current sources through the one or more electrodes of the first polarity; and returning current from the patient's body to the return terminals of the four constant current sources through the four electrodes of the second polarity.

In some instances, each electrode can be included in no more than one of the functional sets.

The one or more constant current sources can be direct current or alternating current sources. At any particular time during operation, however, each terminal of the one or more constant current sources is acting as either a supply terminal or a return terminal.

The method can include, for example, monitoring an electrical resistance between the supply terminal and return terminal for one or more of the constant current sources while current is being delivered by the one or more constant current sources to the patient. The method can include, for example, monitoring a voltage being produced across the constant current source's supply and return terminals to provide at least an indirect measure of resistance (and other information about system operation and/or configuration).

In response to one of the monitored voltage exceeding a threshold value, the method can include reducing an amount of current passing through a corresponding one of the electrodes; and increasing an amount of current being delivered at a different one or more of the electrodes by an amount approximately equal to the amount of current that is reduced. Typically, a rate of change associated with reducing or increasing the amounts of current flowing is limited (either manually or automatically) to no more than approximately 1 milliamp per second.

Typically, if shifting of current occurs, the electrodes or electrodes that experience an increase in the amount of current flowing are in the same functional set as the electrode or electrodes that experience a reduction in the amount of current flowing.

In a typical implementation, a desired therapeutic effect can be achieved as long as the electric field strength produced by the current flow at any location within the target tissue is not changed by more than approximately 50%, or wherein a peak electric field in the brain is not changed by more than 15%, or wherein an area of cortical surface that is greater than 50%, 75%, or 90% or the peak cortical field does not change more than 10 cm2, or wherein an average electric field in the target tissue does not change by more than approximately 50% OR any combination of the foregoing.

In another aspect, a system includes a plurality of electrodes and one or more constant current sources, each having a supply terminal and a return terminal. Typically, the current being supplied at the supply terminal at any given time is equal to current being returned to the return terminal. The electrodes can be coupled to a patient's head to form one or more functional sets. Each functional set has two or more electrodes arranged such that a desired therapeutic effect can be achieved when the two or more electrodes deliver a total amount of current to the patient (combined) regardless of what portion of the total amount of current each respective electrode in the functional set delivers. A conductive element couples the constant current source(s) to the electrode(s) such that each supply terminal and each return terminal is coupled to no more than the electrodes of a single one of the functional sets, if any, or to a single one of the electrodes not included in one of the functional sets.

In some implementations, more than one of the supply terminals can be coupled to the electrodes of a single one of the functional sets and/or more than one of the supply terminals is coupled to a single one of the electrodes not part of one of the functional sets, and/or more than one of the return terminals is coupled to the electrodes of a single one of the functional sets, and/or more than one of the supply terminals is coupled to a single one of the electrodes not part of one of the functional sets.

Each constant current source can be adapted to deliver a substantially constant (but adjustable) amount of current to all of the electrodes in a functional set; or to a single electrode that is not part of one of the functional sets.

The system typically includes at least one functional set and/or at least one electrode not part of one of the functional sets.

In some implementations, the one or more functional sets are defined based on one or more of the following factors: physical proximity of same polarity electrodes to one another, electrical resistance between adjacent same polarity electrodes; and/or physical arrangement of electrodes having a first polarity relative to electrodes of a second polarity.

The functional set(s) can include, for example, a pair of same polarity electrodes that are less than about 4 centimeters, more preferably less than about 2 centimeter of one another and most preferably touching one another. The functional set(s) can include, for example, a pair of same polarity electrodes with a resistance between them through the patient of less than about less than about a same polarity electrode. The functional set(s) can include, for example, one electrode or a plurality of same polarity electrodes surrounded by three or more electrodes having an opposite polarity.

According to some implementations, the system includes an adapter electrically coupled to one of the constant current sources and to a group of the electrodes. The adapter has a pair of input conductors, each input conductor adapted to be electrically coupled to an associated one of the supply terminal or return terminal on the constant current source and three or more output conductors, each output conductor adapted to be electrically coupled to an associated one of the electrodes. At least one of the output conductors is electrically connected to one of the input conductors and at least two of the output conductors is electrically connected to the other of the input conductors.

In certain embodiments, the adapter has five (or more) output conductors, one of which is electrically connected to a first of the input conductors and four (or more) of which are electrically connected to a second of the input conductors. However, the adapter can have any number of output conductors connected in any way to the two input conductors.

In some implementations, a resistance meter is in the adapter to measure a resistance between at least some of the output conductors through an external electrical circuit that includes, for example, the patient.

In certain systems with no functional sets, the number of electrodes is sometimes equal to (or no more than) the number of supply or return terminals connected to one or more of the electrodes to deliver current minus a number of supply or return terminals that share an electrode plus a number of electrodes that are connected to more than one supply or return terminal. In some implementations, there are no unused current sources or terminals of current sources in the system. This typically means that all of the current sources are connected and supplying a significant amount of current to one or more electrodes.

In certain systems that include no functional sets, the number of supply and return terminals connected to one or more of the electrodes is two times the number of electrodes minus the number of electrodes that are connected to more than one supply or return terminal, minus N, where N is a number of electrodes that are added to the system by virtue of one or more passive-splitting interface devices being coupled to one or more of the supply and return terminals. Each passive-splitting interface device typically has the ability to measure resistance across each pair of electrodes extending out of the passive-splitting interface device.

In certain systems, where every electrode in the system is part of a functional set, the number of functional sets is equal to the number of supply or return terminals connected to one or more of the functional sets to deliver current minus a number of supply or return terminals that share a functional set plus a number of functional sets that are connected to more than one supply or return terminals. In some of such systems, there are no unused current sources or terminals in the system.

In certain systems, if all of the electrodes in the system are in a functional set, and the electrodes in a functional set are divided into two or more groups, with one or more electrodes in each group, each group can be connected to a single one of the supply or return terminals, and for each functional set, the number of groups formed is equal to a number of redundant supply or return terminals plus 1.

In another aspect, a device includes a pair of input conductors, each input conductor adapted to be electrically coupled to an associated one of the supply terminal or return terminal on the constant current source and three or more output conductors, each output conductor adapted to be electrically coupled to an associated one of the electrodes. At least one of the output conductors is electrically connected to one of the input conductors and at least two of the output conductors is electrically connected to the other of the input conductors. A resistance meter is provided to measure a resistance between at least some of the output conductors through an external circuit.

In some implementations, the device includes five output conductors, one of which is electrically connected to a first of the input conductors and four of which are electrically connected to a second of the input conductors.

In this document, neurocranial stimulation and/or electrostimulation refers broadly to any stimulation using an electrode on the head or cranium.

In some implementations, one or more of the following advantages may be present.

For example, a safe and highly effective neurocranial stimulation technique can be realized. Furthermore, the complexity and number of components in a neurocranial stimulation system can be reduced. As such, effective neurocranial therapy can be provided in a highly cost-effective manner. The precision with which neurocranial stimulation can be delivered and the level of control that can be exercised over that delivery is improved. Systems can be realized that adapt in real time to component failures or other systematic problems. This adaptation can be implemented with virtually no impact on the therapeutic effect being delivered by the treatment. The occurrence of patient injuries resulting from neurocranial stimulation can be reduced.

Moreover, an approach is disclosed for determining how may current sources and electrodes are necessary (or needed), if and how to minimize or increase their number, deal with power issues such as the number of power sources, otherwise design them, and further consider electrode properties.

Highly safe and effective brain stimulation techniques are disclosed herein. This includes techniques for configuring electrodes to deliver safe and effective stimulation, particularly in systems involving multiple stimulation sources and/or multiple stimulation electrodes.

BRIEF DESCRIPTION OF THE DRAWINGS

FIGS. 2-10 are schematic diagrams of exemplary neurocranial electrical stimulation systems.

FIG. 16 includes five top schematic views of a patient's head with electrodes attached thereto.

FIG. 22 shows distribution of tangential electric field in a patient's head with an electrode configuration using different stimulation systems.

DETAILED DESCRIPTION

Figure 1:
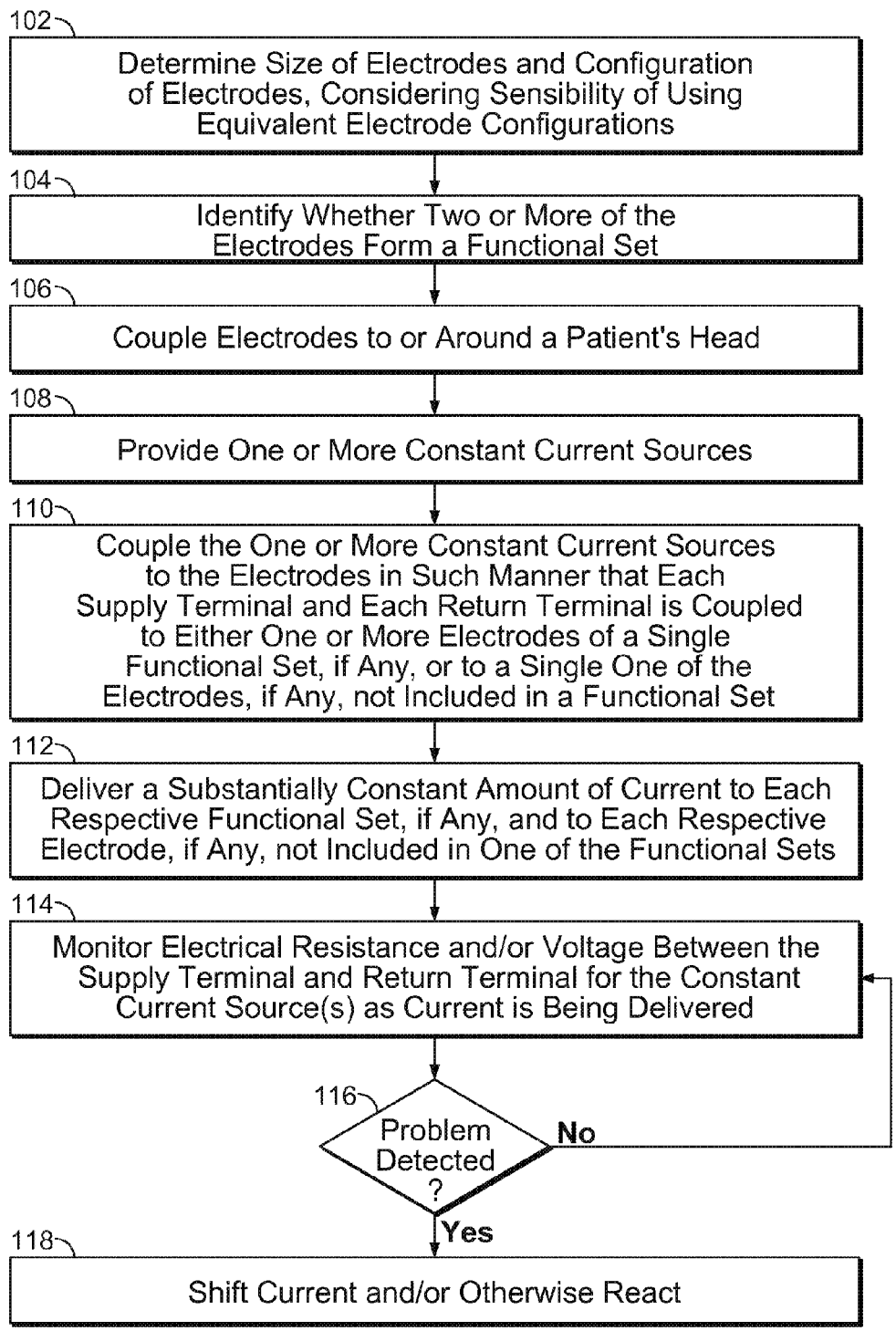
FIG. 1 is a flowchart showing a method of delivering neurocranial electrical stimulation to a patient.

FIG. 1 is a flowchart showing an implementation of a method of delivering neurocranial electrical stimulation to a patient's head as part of a medical treatment regime.

The illustrated method includes determining 102 the size of electrodes to use and the configuration thereof on or around the patient's head in order to effectively deliver neurocranial stimulation. This involves considering the sensibility of reducing the total number of electrodes and/or current sources in the system, if possible, by considering equivalent electrode configurations, as disclosed herein. Equivalent electrode configurations essentially are different electrode configurations that deliver to the patient a substantially identical therapeutic effect, despite the differences.

The illustrated method also includes identifying 104 whether any of the electrodes form what is referred to herein as a functional set. In a typical implementation, a functional set includes two or more electrodes that are arranged on the patient's head such that a desired therapeutic effect can be achieved when the two or more electrodes carry a total amount of current to or from the patient regardless of what portion of the total amount of current each respective electrode in the functional set carries. Thus, the same therapeutic effect, or at least substantially the same therapeutic effect can be achieved regardless of how the current is divided among the two or more electrodes in a functional set. Substantially the same therapeutic effect may include, in some instances, some overlapping or comparative effects. For example, in some instances, even if a condition is treated in a different, but still meaningful way, the therapeutic effect may be considered substantially the same.

In general, a substantially the same therapeutic effect is produced as long as the electric field strength generated by the application of current in a patient's head at any given location in the target tissue is not changed by more than about 50% (including not more than about 40%, not more than about 30%, not more than about 20% and not more than about 10%). The target tissue can be defined as the area in the patient's head or brain that is being targeted for treatment.

In a typical implementations, a "target tissue" is a specific one or more tissues or areas of tissue in the patient's brain, but not necessarily the whole brain, that the current being delivered to the patient's head is intended to treat. Generally the target tissue will be defined or indicated by reference to a volume or an area where a specific function or pathology is localized. In one embodiment, the target tissue is located in the brain periphery, in a region near the cranium surface, or in a region proximal to the skull. Target tissue may include motor regions or sensory regions or processing regions or cognitive regions. In one embodiment, the target tissue is specific by gyri or gyrus, including when a specific gyri or gyrus are linked with a specific function or pathology. The target tissue may be specified by reference of standard anatomical coordinate or regions. In one embodiment, the target tissue is identified with assistance of an individualized anatomical model or scan. Some methods of imaging and segmentation, that illustrate but by no means restrict suitable anatomical modeling, are illustrated in the exemplary embodiment. In cases where stroke damage, traumatic brain injury, or other malformation is evident under anatomical images, then this information may be used to guide stimulation and identify targets including peri-stroke and peri-damaged regions which are regions around the presumed damaged region, each of which, under various situations may be considered a target tissue. For example in stroke is may be desired to activate pre-regions to enhance recovery.

In one embodiment, the target tissue is identified with the assistance of a functional imaging system such as an fMRI or EEG, either in a patient specific manner or by referencing population averages. Such functional imaging may be combined with a task (e.g. reaching, thinking, cognitive challenge, physical task) or sensory input (e.g. tactile, visual, audio) to assist in localizing a target tissue region of interest. Such tasks and stimuli may be specific to the predicted pathology or the region of interest. For example, the process or region which stimulation is intended to treat or target is activated by the task or sensory input, and then stimulation is applied to target the activated region. In one embodiment, the target tissue is selected incorporating a range of information linking a specific brain region to pathology either 1) as the function of the brain region may be compromised and/or 2) as activation of the region may facilitate treatment. For example, for the treatment of some conditions related to acute pain or chronic pain motor regions may targeted. For example, for the treatment of chronic schizophrenia, the target tissue may be the left dorsolateral prefrontal cortex. For example, for the treatment of depression or addiction the target tissue may be one or more of the pre-frontal regions. For example, for Alzheimer's, depression, tinnitus and epilepsy, the target tissue may include the front-lateral brain region. For learning stimulation, the target tissue may be the motor or frontal regions. For visual learning, visual modulation, or recovery of visual function the target tissue may be the occipital lobe and sub-regions therein. For fear extinction the target tissue may be the ventro-medial pre-frontal cortex. For language disability the target tissue may include frontal regions. For epilepsy treatment the target tissue may be the temporal lobe, hippocampus, or cortical region associated with the seizure focus. The insula or frontal regions may be the target tissue for addiction, smoking cessation, obesity and cravings. The above examples are not intended to be a limited or to be an exclusive list, and additional and modified tissue targets may be identified for specific individuals or diseases by referencing the extensive known literature on brain disease. Target tissue or regions typically indicates a portion of the brain defined by reference to standard anatomical coordinates and regions, sub-regions of these regions, regions formed by combined one or more regions, by functional measures, and/or by individualized parameters. In some implementations, desired therapeutic effect can be achieved as long as the electric field strength produced by the current flow at any location within the target tissue is not changed by more than approximately 50%, or where the peak electric field in the brain is not changes by more than 15%, or where the area of cortical surface that is greater than 50%, 75%, or where 90% or the peak cortical field does not change more than 10 cm2, or wherein the average electric field in the target tissue does not change by more than approximately 50%, or any combination of the above.

If, for example, three electrodes form a functional set, then the same, or substantially the same, therapeutic effect can be achieved, as long as a total amount of current (e.g., X milliamps, where X is any number) is being delivered by the three electrodes in any combination. For example, the same, or substantially the same, therapeutic effect can be produced regardless of whether each electrode is supplying X/3 milliamps, or two electrodes are each delivering X/2 milliamps with the third electrode delivering no current, or one electrode delivering X milliamps and the other two delivering no current. Indeed, regardless of how the current (X milliamps) is divided among the electrodes, the same, or substantially the same, therapeutic effect is produced.

Identifying functional sets can be a relatively simple process or can be considerably more complex depending on requirements of different applications. In general, there are a variety of factors that can influence whether or not electrodes placed on the patient's head form one or more functional sets. These factors include, for example, one or more of the following: the physical size and shape of the electrodes under consideration, their locations on the patient's head, the distance between the electrodes under consideration, the resistance between adjacent electrodes on the patient's head, the amount of current the electrodes under consideration will deliver, the polarity (e.g., whether they supply current to the patient or return current from the patient or both) of the electrodes under consideration, the polarity, size, shape and location of any electrodes surrounding the electrodes under consideration, the distance between the electrodes under consideration and neighboring electrodes. Essentially, in various implementations, one or more of these, and other factors, may be considered in identifying whether any of the electrodes form a functional set.

More often than not, a functional set exists when the electrical resistance, measured through the patient, between a pair of same polarity electrodes (i.e., electrodes that either both supply current or both return current at the same time) is less than about 1 kOhm, preferably less than about 200 ohms, less than about 100 Ohms, less than about 10 Ohms, less than about 1 Ohm or close to zero ohms. Additionally, more often than not, a functional set exists when the distance between a pair electrodes having the same polarity on the patient's head is less than about 4 centimeters, more preferably less than about 2 centimeter of one another and most preferably touching one another.

A functional set can exist if a single electrode or multiple electrodes having the same polarity are at least substantially surrounded by two or more electrodes having an opposite polarity. In some implementations, the term "surrounded by" means located on approximately opposite sides of. In some implementations, the term "surrounded by" means that, if three or more electrodes were connected to one another by approximately straight imaginary lines, then those imaginary lines would contact or define an inner space that contains a single or multiple electrodes. In a particular example, one or more electrodes having a first polarity form a functional set by virtue of being surrounded by four electrodes of a second polarity that is different than the first polarity.

In some implementations, the identification of functional sets is performed before the electrodes are coupled to the patient's head. In such implementations, the identification of functional sets can be part of a planning process for where to place the electrodes on the patient's head. In other implementations, identifying the functional sets is performed while the electrodes are being placed upon the patient's head or shortly thereafter.

In various implementations, identifying functional sets can include consideration of one or more of the following factors: electrode configuration, connectivity, desired outcomes, safety concerns, and other issues.

One example of a functional set is where, during the course of stimulation (or during a designated period of stimulation), at any instant, all of the electrodes in the functional set have the same polarity (in the sense that they are all functioning as either sources or sinks) or have zero current, at any instant the total current being delivered to all of the electrodes in the functional set is called the total functional set current at that instant, the current being delivered to each electrode in the functional set is between 0 Amps and the total functional set current, some amount of current may be reduced from one electrode in the set and this exact amount shifted to another electrode in the set such that the total functional set current is not changed, and this shift does not impact or reduce the safety and/or efficacy of the particular neurocranial stimulation protocol being applied as specific to the guidelines of that protocol, or where the shift enhances the safety, robustness, reproducibility, or another feature of stimulation.

In some implementations, functional sets can be defined based on the resistance between electrodes in the functional set through the patient's body. In various implementations, different values of resistance may indicate the presence of a functional set. For example, a resistance between electrodes of less than 1 kOhm, 200, ohms, 100 Ohms, 10 Ohms, 1 Ohm or close to zero ohms may indicate that the electrodes under consideration form a functional set. In one embodiment, two or more electrodes placed right next to each other (or touching each other) form a functional set.

A functional set can include multiple electrodes of the same polarity (for an entire stimulation session or for only a defined portion of a stimulation session) surrounded by electrodes of the opposite polarity. In such instances, although the surrounded electrodes form a functional set, the surrounding electrodes do not necessarily form a functional set, although they could potentially form a separate functional set. In this example, the inner functional set may be positioned on the scalp in a manner to target a specific brain region, for example a region under the scalp.

Other ways that functional sets may be formed include having electrodes that are touching, connected to one another by a cable, connected to one another by a conductive gel or otherwise forming a relatively low resistance conductive path therebetween. Electrodes can form a functional set by being mechanically connected to one another, for example, by a flexible band or specialized holder. Electrodes in a functional set may be attached to a mechanical mechanism(s) such that the integrity of one electrode is enhanced or reduced in connection with its connectivity.

As another example, in some implementations, two or more electrodes can be considered a functional set where each electrode is connected to its own current source. The current delivered to each electrode can then be independently controlled. There may be configurations where one or more, but not all, of the electrodes within a functional set is connected to its own current source.

In a typical implementation, understanding and applying concepts related to functional sets can improve the safety and efficacy of neurocranial stimulation. In some implementations, when current is shifted between electrodes in a functional set, the original and new current delivery schemes are substantially equivalent from a therapeutic perspective. Additionally, in some implementations, passive Functional Electrode Set indicates two or more electrode forming a Functional Set and connected to a single current source, such that the current from the current source is split within the functional set. However, the specific nature of this split does not reduce safety or efficacy because the electrodes are a Functional Set. Use of passive Functional Sets may have several advantages for Neurocranial stimulation simplicity, robustness, safety, or efficacy including 1) reduced number of current sources; 2) redundancy among electrodes; 3) passive regulation of current splitting where current will automatically divert to the better electrodes.

The illustrated method also includes coupling 106 electrodes to or around the patient's head. In a typical implementation, the electrodes are designed so as to be able to deliver therapeutic amounts of electrical current to the patient's brain. The electrodes can be coupled to the patient head in any conventional manner such as by using a conductive, adhesive material to hold the electrodes in place.

The illustrated method includes providing 108 one or more constant current sources to supply current to the electrodes on the patient's head. A constant current source is an electrical or electronic device or collection of circuit elements that is capable of supplying a constant or substantially constant, but controllable, source of current. The current being supplied can be direct current or alternating current.

In a typical implementation, each constant current source has a pair of terminals. At any given time, one of those terminals acts as a supply terminal while the other acts as a return terminal. During operation, at any given time, the amount of current flowing out of a constant current source's supply terminal is equal to the amount of current flowing into the constant current source's return terminal.

The illustrated method includes coupling 110 the one or more constant current sources to the electrodes. In a typical implementation, this is done in such a manner that each supply terminal and each return terminal is respectively coupled to either: (1) one or more electrodes in a single functional set; or (2) a single one of the electrodes that is not part of a functional set. In a typical implementation, therefore, each supply terminal is coupled to no more than one electrode unless the electrode is part of a functional set, in which case, the supply terminal can be connected to two or more (and up to all) of the electrodes in the functional set. Similarly, in a typical implementation, each return terminal is coupled to no more than one electrode unless the electrode is part of a functional set, in which case, the return terminal can be connected to two or more (and up to all) of the electrodes in the functional set.

With the one or more constant current sources coupled to the electrodes in the foregoing manner, the amount of current delivered to each respective functional set and to electrode that is not part of a functional set, can be controlled and kept relatively constant regardless of how much resistance is in each conductive path (from supply terminal to return terminal).

All of the electrodes in a particular functional set need not be coupled to the same constant current source. Indeed, in some implementations, the electrodes within a particular functional set can be coupled to two or more controlled current sources. In some implementations, every electrode in a particular functional set is coupled to a different controlled current source.

After coupling the constant current sources to the electrodes, the illustrated method includes delivering 112 a substantially constant amount of current to each respective functional set, if any, and to each electrode, if any, that is not part of a functional set. In a typical implementation, the independently controllable, substantially constant current being delivered to the functional sets and/or electrodes not part of a functional set helps enhance the therapeutic effectiveness of a neurocranial electrical stimulation procedure.

The illustrated method includes monitoring 114 the resistance across and/or voltage being supplied across the supply terminal and return terminal for each constant current source while current is being delivered to the patient. The voltage being produced can be indicative of a wide variety of parameters including, for example, resistance of the circuit external to the constant current sources. In some instances, if the monitored voltage exceeded a predetermined value or if there are rapid changes or fluctuations in the monitored voltage, this could be indicative of a problem (e.g., a faulty electrode) in the external circuit. Monitoring the voltage on a continuous or periodic basis can, in some instances, help identify such problems so that corrective measures can be taken.

In some implementations, as long as the monitored voltage does not indicate the existence of a problem in the external circuit, the constant current source continues delivering current to all of the electrodes it is connected to, which can be, for example, two or more electrodes in the same functional set.

If, at 116 in the illustrated flowchart, the monitored voltage does indicate the existence of a problem (e.g., a faulty electrode), then corrective measures 118 are taken. Otherwise, monitoring 114 simply continues while current is being delivered.

According to the illustrated method, if the monitored voltage does indicate a problem in the external circuit (e.g., a faulty electrode), then current is shifted 116 from the faulty electrode to a good electrode within the same functional set as the faulty electrode. The shifting current can be accomplished either automatically or manually. In a typical implementation, the current is shifted automatically from a faulty electrode to a good electrode. Typically, the ability to shift an amount of current stems from a faulty electrode to a good electrode comes from the fact that the faulty electrode and good electrode are coupled to respective independent current sources. This can be the case even if the electrodes in question are part of a functional set.

In response to a problem detected, a user may reconfigure—or the system may automatically reconfigure—the electrodes in accordance with one or more techniques disclosed herein that would result in a configuration that produces a substantially identical therapeutic effect in the patient.

In a typical implementation, detection of a voltage and/or resistance-related problem and/or shifting of current can be followed by or accompanied by the triggering of an alarm.

FIGS. 2-7 are schematic representations of exemplary neurocranial electrical stimulation systems.

FIG. 2, for example, shows a system 200 that includes three electrodes 202a, 202b, 202c coupled (e.g., with a conductive adhesive material) to a patient's skin 205 near a target tissue 204 (e.g., in the patient's head).

The electrodes 202a, 202b, 202c can be any type of medical grade electrode. In some implementations, the electrodes 202a, 202b, 202c are Device Rated Current(I) Voltage Electrodes, referred to herein as "DRIVER" electrodes. Typically, a DRIVER electrode is an electrode that resists failing due to increases in resistance or mechanical failure or the occurrence of some undesired chemical or physical process at the electrode (that could effect skin). DRIVER electrodes are generally rated to allow a specific amount of current flow across them. Ratings can be based on peak current, total charge, current density, charge density, charge per phase, or any characteristic. A system (e.g., system 200) is generally adapted so that it does not deliver a current through an electrode, under any operational circumstances, that exceeds the DRIVER electrode's rating.

The system 200 includes two constant current sources 206a, 206b, each having a pair of terminals (designated A and B), each having opposite polarities at any given time. Each constant current source 206a, 206b is adapted to deliver from a supply terminal and absorb at a return terminal a substantially constant amount of current regardless of the resistance or changes in resistance of the circuit external to the constant current source.

Each terminal is electrically coupled by a conductive element to an associated one of the electrodes 220a, 220b or 220c. In particular, the A terminal of both constant current sources 206a, 206b is coupled to electrode 202b, the B terminal of constant current source 206a is coupled to electrode 202a and the B terminal of constant current source 206b is coupled to electrode 202c.

In the exemplary system 200, none of the electrodes 202a, 202b, 202c form a functional set. Moreover, none of the A or B terminals is connected to more than one electrode. Accordingly, the amount of current being delivered to and returned from each portion of the target tissue 204 can be controlled with precision and maintained relatively constant.

In the illustrated implementation, conductive paths are formed between the A terminal and B terminal of each respective constant current source 206a, 206b. One of these conductive paths, for example, includes A terminal of constant current source 206a, the conductive element that couples the A terminal to electrode 202b, the electrode 202b, the target tissue 204, electrode 202a, the conductive element that couples electrode 202a to the B terminal of constant current source 206a and return terminal 208b.

Each constant current sources is operable so that, at any given moment, the current flowing through its A terminal is equal to, but in an opposite direction as, the current flowing through its B terminal.

The illustrated system 200 includes the minimum number of A and B terminals (i.e., four) to support operation of the three electrodes 202a, 202b, 202c without connecting any of the terminals to more than one electrode 202a, 202b, 202c. Not connecting any of the terminals to more than one electrode 202a, 202b, 202c, unless one or more functional sets are present, helps ensure that independent current control will be available at each electrode.

More generally, the relationship between the number of current source channels required to support a number of electrodes that are not part of a functional set, in some implementations, can be expressed as follows. The number of electrodes (3 in FIG. 2) equals the number of terminals (4 in FIG. 2) minus the number of terminals that share an electrode (2 in FIG. 2) plus the number of electrodes with more than one terminal connected to it (1 in FIG. 2).

Thus, in the illustrated system, the maximum number of electrodes that the current sources can supply with independent control to each electrode is three (i.e., 4−2+1=3), which is the number shown.

FIG. 3 shows a system 300 that is similar to the system 200 of FIG. 2, except that system 300 includes five electrodes 302a-302e coupled to a patient 305 near a target tissue 304 and four constant current sources 306a, 306b, each having an A terminal and a B terminal.

As in FIG. 2, none of the electrodes in FIG. 3 form a functional set. As such, none of the A or B terminals is connected to more than one electrode. Accordingly, the amount of current being delivered to and returned from each portion of the target tissue 304 can be controlled with a high degree of precision and/or can be maintained at a relatively constant level.

Moreover, in the illustrated system 300, the number of electrodes (5 in FIG. 3) equals the number of terminals (8 in FIG. 3) minus the number of terminals that share an electrode (4 in FIG. 3) plus the number of electrodes with more than one terminal connected to it (1 in FIG. 3).

Thus, in the illustrated system, the maximum number of electrodes that the current sources can supply with independent control to each electrode is five (i.e., 8−4+1=5), which is the number shown.

FIG. 4 shows a system 400 that is similar to the system 200 of FIG. 2, except that system 400 includes four electrodes 402a-402d coupled to a patient 405 near a target tissue 404 and three constant current sources 406a, 406b, 406c each having an A terminal and a B terminal.

In FIG. 4, the two center electrodes 402b, 402c are considered a functional set (e.g., by virtue of them being positioned such that they are capable of delivering the same or substantially the same therapeutic effect to the target tissue as long as a given amount of current is being delivered by the electrodes together, regardless of how current is split between them).

Although the two center electrodes 402b, 402c are considered a functional set, they are not connected to the same current source. As such, in the illustrated system 400, the number of electrodes (4 in FIG. 4) equals the number of terminals (6 in FIG. 4) minus the number of terminals that share an electrode (4 in FIG. 3) plus the number of electrodes with more than one terminal connected to it (2 in FIG. 4). Thus, in the illustrated system, the number of electrodes that the current sources can supply with independent control to each electrode is four (i.e., 6−4+2=4), which is the number shown.

FIG. 5 shows a system 500 that is similar to the system 400 of FIG. 4, except that system 500 has three electrodes 502a-502c near the target tissue instead of four. Moreover, the system 500 has three constant current sources 506a, 506b, 506c each having an A terminal and a B terminal.

In FIG. 5, from a functional perspective, the center electrode 502b is substantially similar to the two center electrodes 402b, 402c in FIG. 4.

In the illustrated system 500, the number of electrodes (3 in FIG. 5) equals the number of terminals (6 in FIG. 5) minus the number of terminals that share an electrode (5 in FIG. 5) plus the number of electrodes with more than one terminal connected to it (2 in FIG. 4). Thus, in the illustrated system, the number of electrodes that the current sources can supply with independent control to each electrode is three (i.e., 6−5+2=3), which is the number shown.

FIGS. 6-10 are schematic representations showing exemplary configurations for arrays of electrodes on a patient's head. Each of these respective figures shows two different electrode configurations, side-by-side, that are substantially equivalent to one another from the perspective of therapeutic effectiveness. That is, each configuration can produce a substantially identical therapeutic effect in a patient as long as substantially the same total amount current is being delivered to the patient in each instance.

Figure 6:
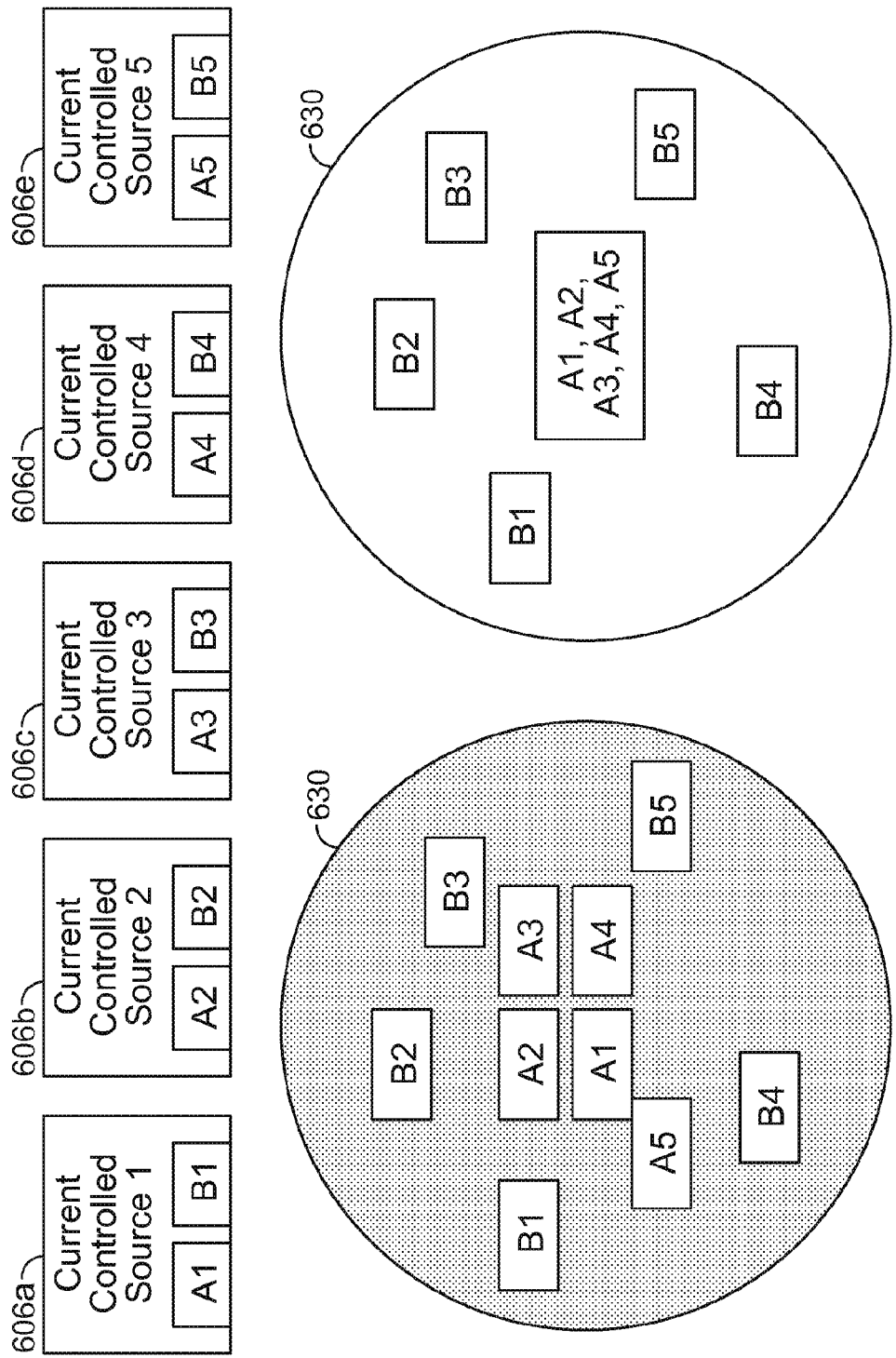

FIG. 6, in particular, is a schematic representation of a system that includes five constant current sources 606a-606e, each of which has a pair of terminals 608a, 608b. The terminals of the constant current sources are designated as A1, B1, A2, B2, A3, B3, A4, B4, A5 and B5, respectively. In a typical implementation, all of the terminals designated with the letter "A" are of the same polarity at any given time during circuit operation. Similarly, in a typical implementations, all of the terminals designated with the letter "B" are of the same polarity at any given time during circuit operation.

Two alternative, but substantially equivalent, electrode configurations are shown below the five constant current sources 606a-606e and are arranged side-by-side relative to each other. The alternative electrode configurations are considered substantially equivalent configurations because the therapeutic effect produced by each configuration is substantially the same as long as the total amount of current delivered to the patient is substantially the same. In each configuration, multiple electrodes are coupled to a patient's head 630.

Each electrode is designated with one or more of the constant current sources' terminal designations (i.e., A1, B1, A2, B2, A3, B3, A4, B4, A5, B5). This designation scheme indicates which electrode is coupled to which terminal. So, for example, in the shaded configuration (on the left side of the page), the five centrally-disposed electrodes are respectively coupled to terminals A1, A2, A3, A4 and A5, whereas the five peripherally-disposed electrodes, which substantially surround the centrally-disposed electrodes, are coupled to terminals B1, B2, B3, B4 and B5, respectively. Likewise, in the unshaded configuration (on the right side of the page), a single centrally-disposed electrode is coupled to all of the constant current source terminals (i.e., A1, A2, A3, A4 and A5), whereas the five peripherally-disposed electrodes, which substantially surround the single centrally-disposed electrode, are coupled to terminals B1, B2, B3, B4 and B5, respectively.

In the unshaded configuration (on the left side of the page), the five centrally-disposed electrodes, respectively designated A1-A5, can be considered a single functional set. This may be, for example, by virtue of their relatively close proximity to one another and/or the fact that they are substantially surrounded by a group of opposite polarity electrodes (i.e., those electrodes designated B1-B5). The unshaded configuration (on the right side of the page) is substantially equivalent, from a therapeutic perspective, to the shaded configuration (on the left side of the page).

Either of the two electrode configurations may be implemented in various circumstances. For example, with the shaded configuration (on the left side of the page), a separate, independent constant current source can be connected to each of the five centrally-disposed electrodes (designated A1, A2, A3, A4 and A5). This type of arrangement may be desirable, for example, because in the event that one or more of the centrally-disposed electrodes failed (or became somehow compromised), current could easily be shifted to one or more of the other centrally-disposed electrodes to compensate for the failed (or somehow compromised) electrode. If the five centrally-disposed electrodes truly were a functional set, then this shifting of current from the failed electrode to one or more of the good electrodes would make substantially no difference to the therapeutic effectiveness of the treatment regime. On the other hand, the unshaded configuration (on the right side of the page) may be considered to be a simpler and less expensive configuration, due to the lesser number of electrodes, than the shaded configuration.

Figure 7:
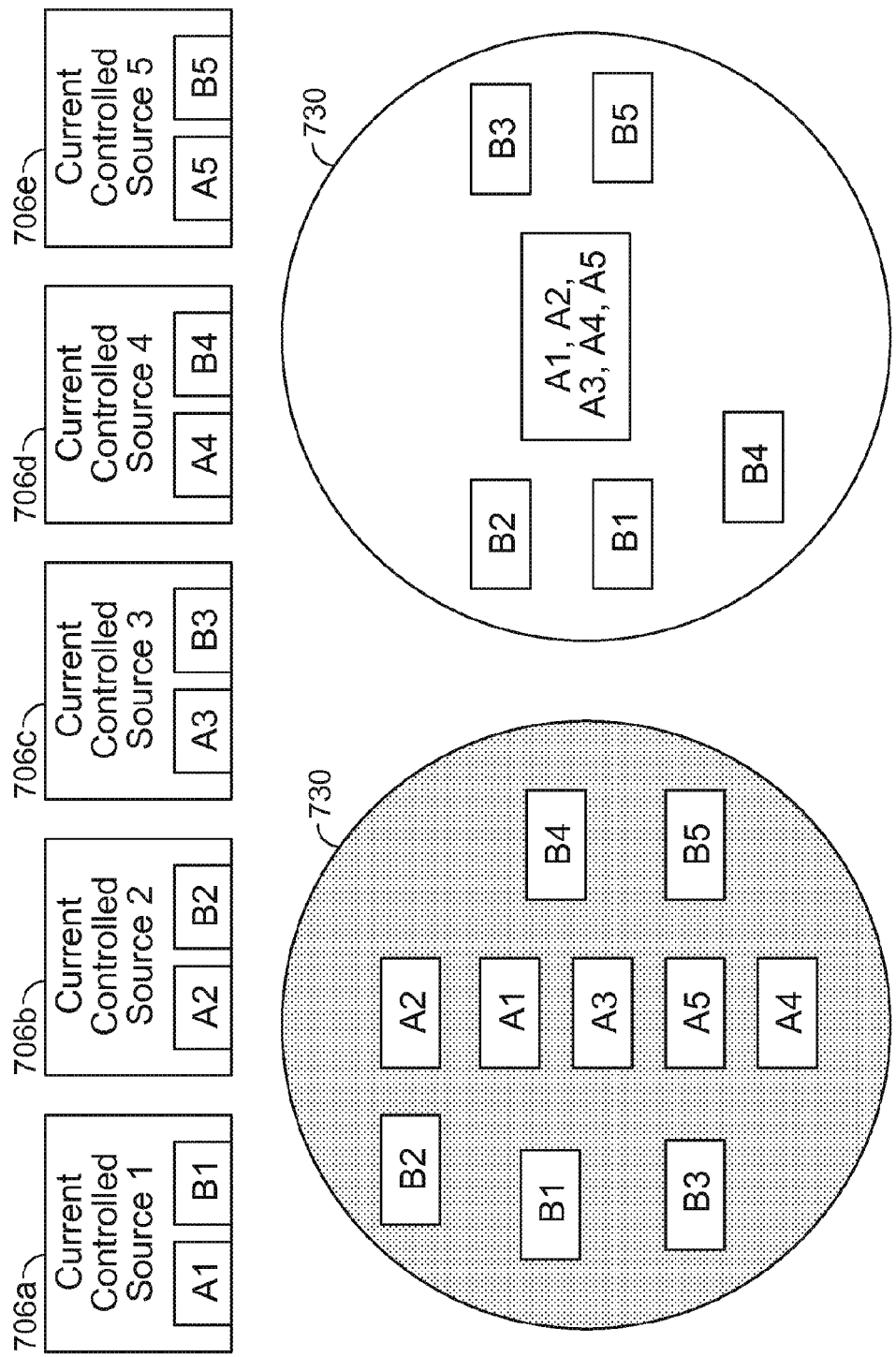

FIG. 7 is similar to FIG. 6 except the particular arrangement of electrodes in each of the shaded (left side of the page) and unshaded (right side of the page) configurations in FIG. 7 is different than in FIG. 6.

In each system configuration represented in FIG. 7, there are five constant current sources 706a-706e, each of which has a pair of terminals 708a, 708b. As in FIG. 6, the terminals of the constant current sources are designated as A1, 81, A2, B2, A3, B3, A4, B4, A5 and B5, respectively.

Two alternative, but substantially equivalent, electrode configurations are shown below the five constant current sources 706a-706e and are arranged side-by-side relative to each other. The alternative electrode configurations are considered substantially equivalent configurations because the therapeutic effect produced by each configuration if substantially the same amount of current is passed through the patient. In each configuration, multiple electrodes are coupled to a patient's head 730.

Each electrode is designated with one or more of the constant current sources' terminal designations (i.e., A1, B1, A2, B2, A3, B3, A4, B4, A5, B5). This designation scheme indicates which electrode is coupled to which terminal. So, for example, in the shaded configuration (on the left side of the page), the five, centrally-disposed electrodes that aligned like a strip, are respectively coupled to terminals A1, A2, A3, A4 and A5, whereas the five peripherally-disposed electrodes, which form two strips that substantially surround the centrally-disposed electrodes, are coupled to terminals B1, B2, B3, B4 and B5, respectively. Likewise, in the unshaded configuration (on the right side of the page), a single centrally-disposed electrode is coupled to all of the constant current source terminals (i.e., A1, A2, A3, A4 and A5), whereas the five peripherally-disposed electrodes, which substantially surround the single centrally-disposed electrode, are coupled to terminals B1, B2, B3, B4 and B5, respectively.

In some implementations, strips of electrodes can be helpful in targeting certain strip-shaped targets, such as gyri.

In the unshaded configuration (on the left side of the page), the five aligned centrally-disposed electrodes, respectively designated A1-A5, can be considered a single functional set. This may be, for example, by virtue of their relatively close proximity to one another and/or the fact that they are substantially surrounded by two aligned strips of opposite polarity electrodes (i.e., those electrodes designated B1-B5). The unshaded configuration (on the right side of the page) is substantially equivalent, from a therapeutic perspective, to the shaded configuration (on the left side of the page).

As discussed above with reference to FIG. 6, either of the two electrode configurations may be implemented in various circumstances.

Figure 8:
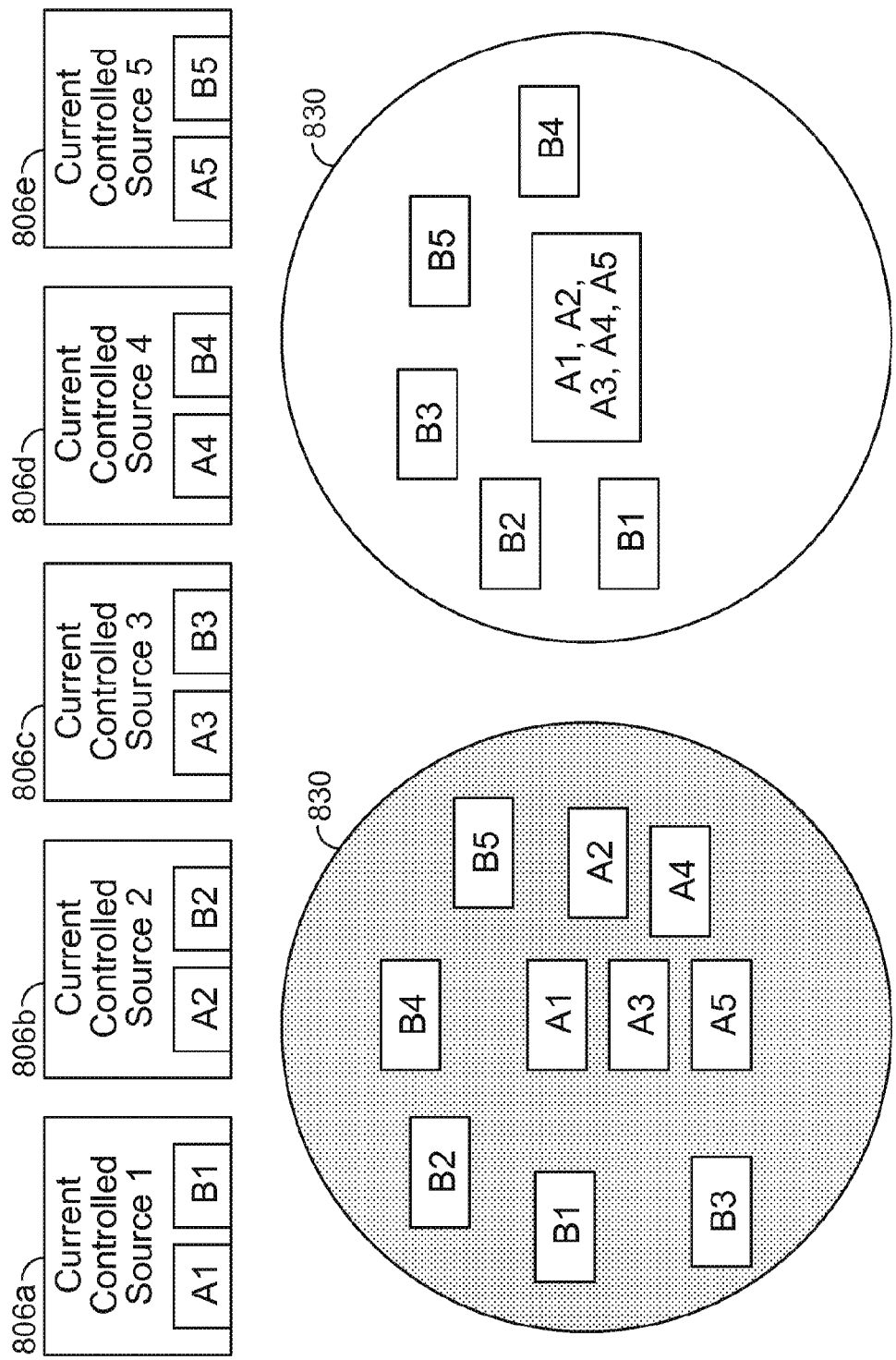

FIG. 8 is similar to FIG. 7 except the particular arrangement of electrodes in each of the shaded (left side of the page) and unshaded (right side of the page) configurations in FIG. 8 is different than in FIG. 7.

In each system configuration represented in FIG. 8, there are five constant current sources 806a-806e, each of which has a pair of terminals 808a, 808b. As in FIG. 7, the terminals of the constant current sources are designated as A1, B1, A2, B2, A3, B3, A4, B4, A5 and B5, respectively.

Two alternative, but substantially equivalent, electrode configurations are shown below the five constant current sources 806a-806e and are arranged side-by-side relative to each other. The alternative electrode configurations are considered substantially equivalent configurations because the therapeutic effect produced by each configuration if substantially the same amount of current is passed through the patient. In each configuration, multiple electrodes are coupled to a patient's head 830.

Each electrode is designated with one or more of the constant current sources' terminal designations (i.e., A1, B1, A2, B2, A3, B3, A4, B4, A5, B5). This designation scheme indicates which electrode is coupled to which terminal. So, for example, in the shaded configuration (on the left side of the page), the five that are tightly-grouped together in the lower right corner of the shaded region, are respectively coupled to terminals A1, A2, A3, A4 and A5, whereas the five electrodes that form an approximately C-shaped pattern that substantially surrounds the five tightly-grouped electrodes, are coupled to terminals B1, B2, B3, B4 and B5, respectively. Likewise, in the unshaded configuration (on the right side of the page), a single centrally-disposed electrode is coupled to all of the constant current source terminals (i.e., A1, A2, A3, A4 and A5), whereas the five electrodes that form an approximately C-shaped pattern that substantially surrounds the single centrally-disposed electrode, are coupled to terminals B1, 82, B3, B4 and B5, respectively.

In the unshaded configuration (on the left side of the page), the five tightly-grouped electrodes, respectively designated A1-A5, can be considered a single functional set. This may be, for example, by virtue of their relatively close proximity to one another and/or the fact that they are substantially surrounded by the approximately C-shaped pattern of opposite polarity electrodes (i.e., those electrodes designated B1-B5). The unshaded configuration (on the right side of the page) is substantially equivalent, from a therapeutic perspective, to the shaded configuration (on the left side of the page).

As discussed above with reference to FIGS. 6 and 7, either of the two electrode configurations may be implemented in various circumstances.

In some instances, equivalent electrode configurations can be realized by replacing two or more outer peripheral electrodes that are close to one another, but participate in surrounding electrodes of another polarity, with a single outer peripheral electrode. This is generally permissible where the therapeutic effect produced by delivering an equal amount of total current by each configuration is substantially the same.

Figure 9:
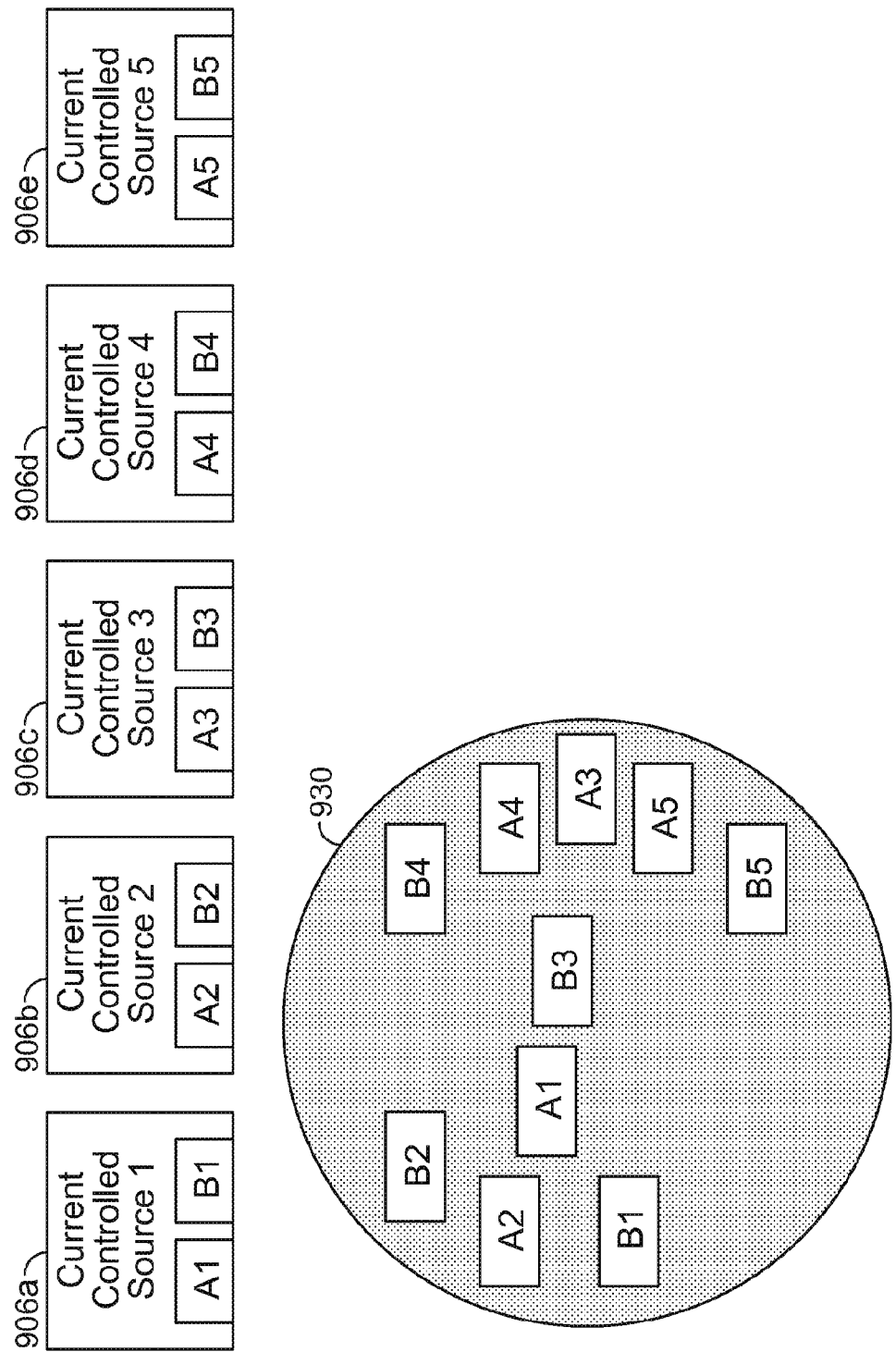

FIG. 9 shows a configuration of electrodes on a patient's head 930 that includes a pair of same polarity electrodes (designated A1 and A2) substantially surrounded by three opposite polarity electrodes (designated as B1, B2 and B3). In some instances, this pair of same polarity electrode (designated A1 and A2) could be considered a functional set and be replaced, for example, by a single electrode at approximately the same location as (or between) the pair of electrodes. Alternatively, in some implementations, this pair of electrodes could be coupled to a single current source, without compromising the circuit's ability to deliver safe and effective therapeutic current delivery to a patient.

Similarly, the electrode configuration in FIG. 9 shows three same polarity electrode (designated A3, A4 and A5) tightly-grouped and substantially surrounded by three opposite polarity electrodes (designated as B3, B4 and B5, which form an approximately c-shaped pattern that partially encloses the A3, A4 and A % electrodes). In some instances, the three electrodes designated A3, A4 and A5 could be considered a functional set and be replaced, for example, by a single electrode at approximately the same location as (or between) the electrodes. Alternatively, in some implementations, the three electrodes designated A3, A4 and A5 could be coupled to a single current source, without compromising the circuit's ability to deliver safe and effective therapeutic current delivery to a patient.

Figure 10:
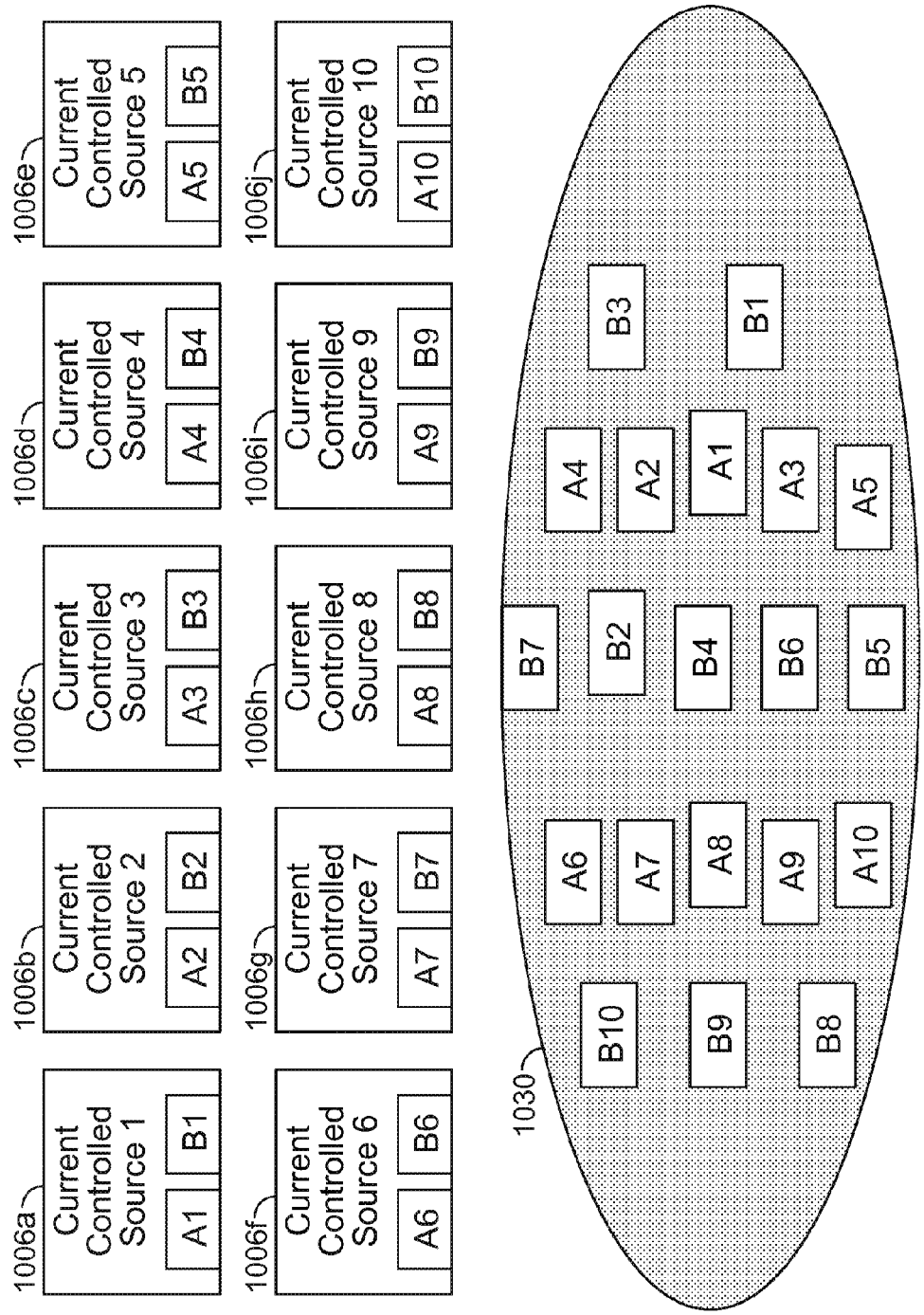

FIG. 10 is similar to FIG. 9 except the particular arrangement of electrodes in FIG. 10 is different than in FIG. 9.

FIG. 10 shows a system that includes a plurality of constant current sources 1006a-1006j connected to a configuration of electrodes that includes a two strips of electrodes (A1-A5 and A6-A10, respectively) of a first polarity substantially surrounded and separated from each other by three strips of electrodes (B1, B3 and B2, B4, B5, B6, B7 and B8, B9, B10) having a second (opposite) polarity. In some instances, each strip of first polarity electrodes could be considered a functional set and be replaced, for example, by a single electrode at approximately the same location as (or somewhere along) the strip. Alternatively, in some implementations, each strip of electrodes could be coupled to a single current source, respectively, without compromising the circuit's ability to deliver safe and effective therapeutic current delivery to a patient.

There are a variety of other situations and electrode configurations that give rise to the possibility of one or more simpler, alternative, substantially identical (from a therapeutic perspective) configurations being possible.

In a typical implementation, therefore, a functional set can be understood as having two or more electrodes arranged such that a desired therapeutic effect can be achieved (or substantially achieved) when the two or more electrodes deliver a total amount of current to the patient regardless of what portion of the total amount of current each respective electrode in the functional set delivers. In a typical implementation, a conductive element can be provided and connected such that each supply terminal and each return terminal is coupled to no more than the electrodes of a single functional set, if any exists, or to a single electrode not included in a functional set.

In a various implementations of a system having multiple constant current sources and multiple electrodes, the constant current sources' supply and return terminals can be coupled to electrodes in one or more of the following ways: more than one supply terminal can be coupled to all (or at least more than one) of the electrodes in a functional set, each supply terminal can be coupled to a single one of the electrodes that are not in a functional sets, each return terminal can be coupled to all (or at least more than one) of the electrodes in a functional set and/or more than one of supply terminal can be coupled to a single electrode that is not part of a functional set.

In a particular implementation, each constant current source is adapted to deliver a substantially constant, but controllable, amount of current to all of the electrodes in a functional set and/or to each single electrode that is not part of one of the functional sets. Some of such systems include one or more functional sets and one or more electrodes that are not part of a functional sets.

Figure 11:
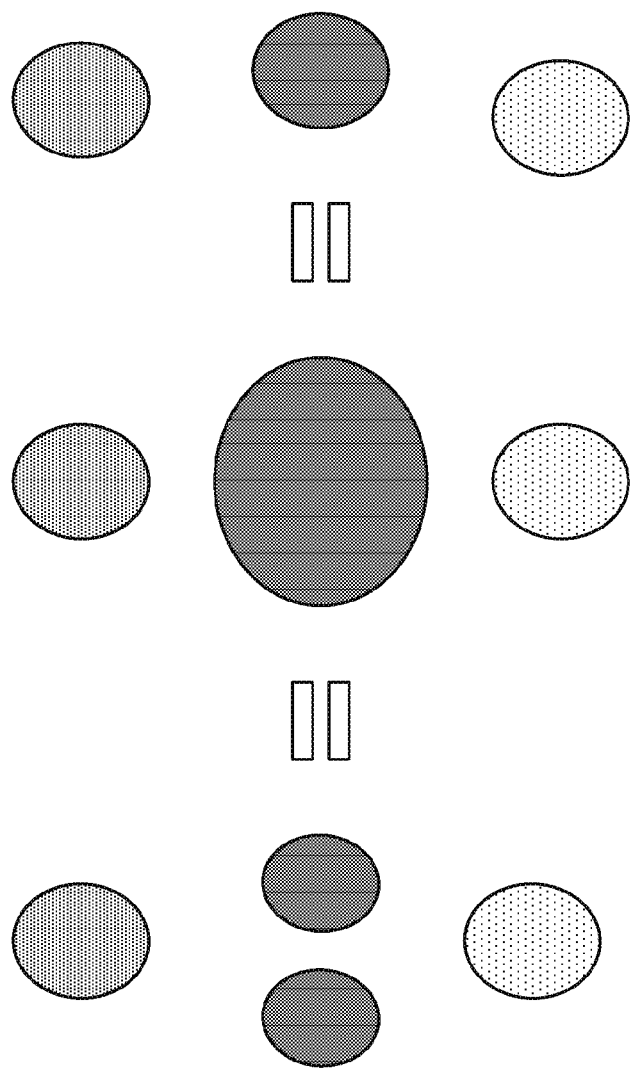
FIG. 11 is a schematic representation of equivalent electrode configurations.

FIG. 11 shows three electrode configurations that can be considered at least substantially equivalent to one another from the perspective of therapeutic effectiveness. The top configuration shows three electrodes. In the top configuration, the middle electrode is approximately the same size as the outer two electrodes and has an opposite polarity as the outer two electrodes.

The middle configuration in FIG. 11 can be considered substantially identical to the top configuration as long as it is used to deliver substantially the same amount of current to the patient as the top configuration. In some implementations, therefore, it may be desirable to replace a configuration of electrodes, such as that shown in the upper configuration, with a configuration of electrodes such as shown in the middle configuration to reduce the current density of current that flows in the middle electrode. In the middle configuration, the middle electrode provides for a lower current density, which could improve a patient's comfort level.

The lower configuration in FIG. 11 shows an electrode configuration that is similar to the electrode configurations in the upper and middle configurations, except that the lower configuration has a pair of middle electrodes, instead of just one electrode. In some implementations, this pair of middle electrodes is considered a functional set as the therapeutic effect of passing current through the pair of middle electrodes would be substantially the same regardless of how the current flow is divided among the middle electrodes.

Figure 12:
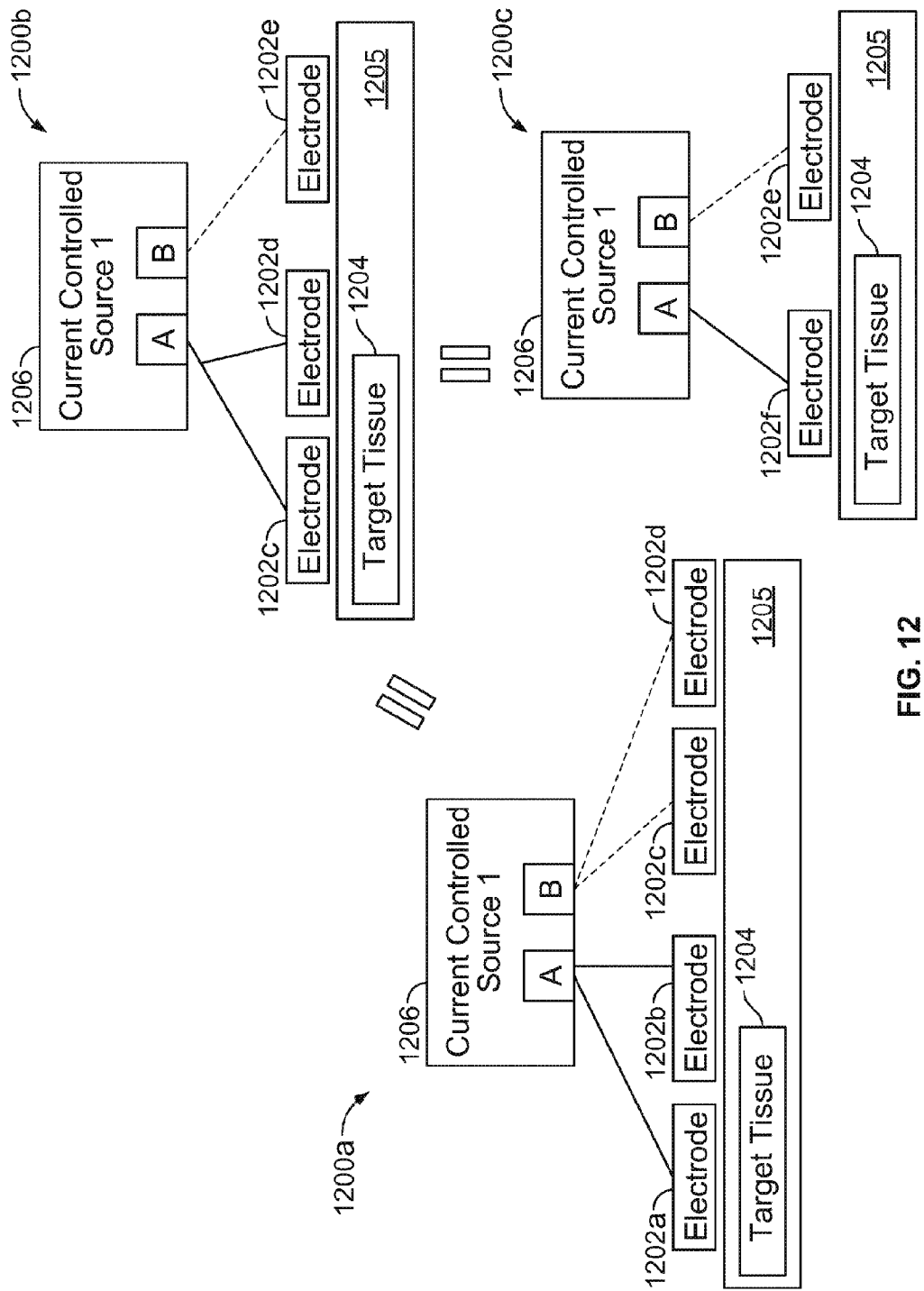
FIG. 12-14 are schematic representations of equivalent system configurations.

FIG. 12 shows schematic representations of exemplary substantially equivalent neurocranial electrical stimulation systems.

The first system 1200a is substantially equivalent to the second system 1200b, which is substantially equivalent to the third system 1200c. This is because as long as the total amount of current delivered to the patient in each system is substantially the same, then the therapeutic effect of delivering that current will be substantially the same.

Each system includes a single constant current source 1206 adapted to deliver current to a target tissue 1204 in a patient 1205.

In the first system 1200a, the electrodes 1202a, 1202b that are coupled to terminal A of the constant current source 1206 form a functional set and the electrodes 1202c, 1202d that are coupled to terminal B of the constant current source 1206 for another functional set. As such, the combined amount of current that is passed through electrodes 1202a, 1202b and the combined amount of current that is passed through electrodes 1202c, 1202d is what matters from a therapeutic perspective, not how that total amount of current is divided between electrodes 1202a and 1205b or 1202c and 1202d. As such, electrodes 1202a and 1202b can be connected to the same terminal (i.e., A) of constant current source 1206 and electrodes 1202c, 1202d can be connected to the same terminal (i.e., B) of constant current source 1206 without concern about which electrode may be carrying more or less of the current.

Since electrodes 1202c and 1202d are a functional set, they can be replaced with a single electrode 1202e, as shown in system 1200b. In a typical implementation, the system 1200b and the system 1200a produce substantially the same therapeutic effect as one another as long as they are delivering substantially the same total amount of current to the patient.

Similarly, since electrodes 1202a and 1202b are a functional set, they can be replaced with a single electrode 1202f, as shown in system 1200c. In a typical implementation, the system 1200c and the systems 1200a and 1200b produce substantially the same therapeutic effect as one another as long as they are delivering substantially the same total amount of current to the patient.

Moreover, the electrode 1202f in system 1200c is larger than either of the electrodes 1202a or 1202b it replaced. This, too, will generally have no substantial negative impact on the therapeutic effect of current delivery.

Figure 13:
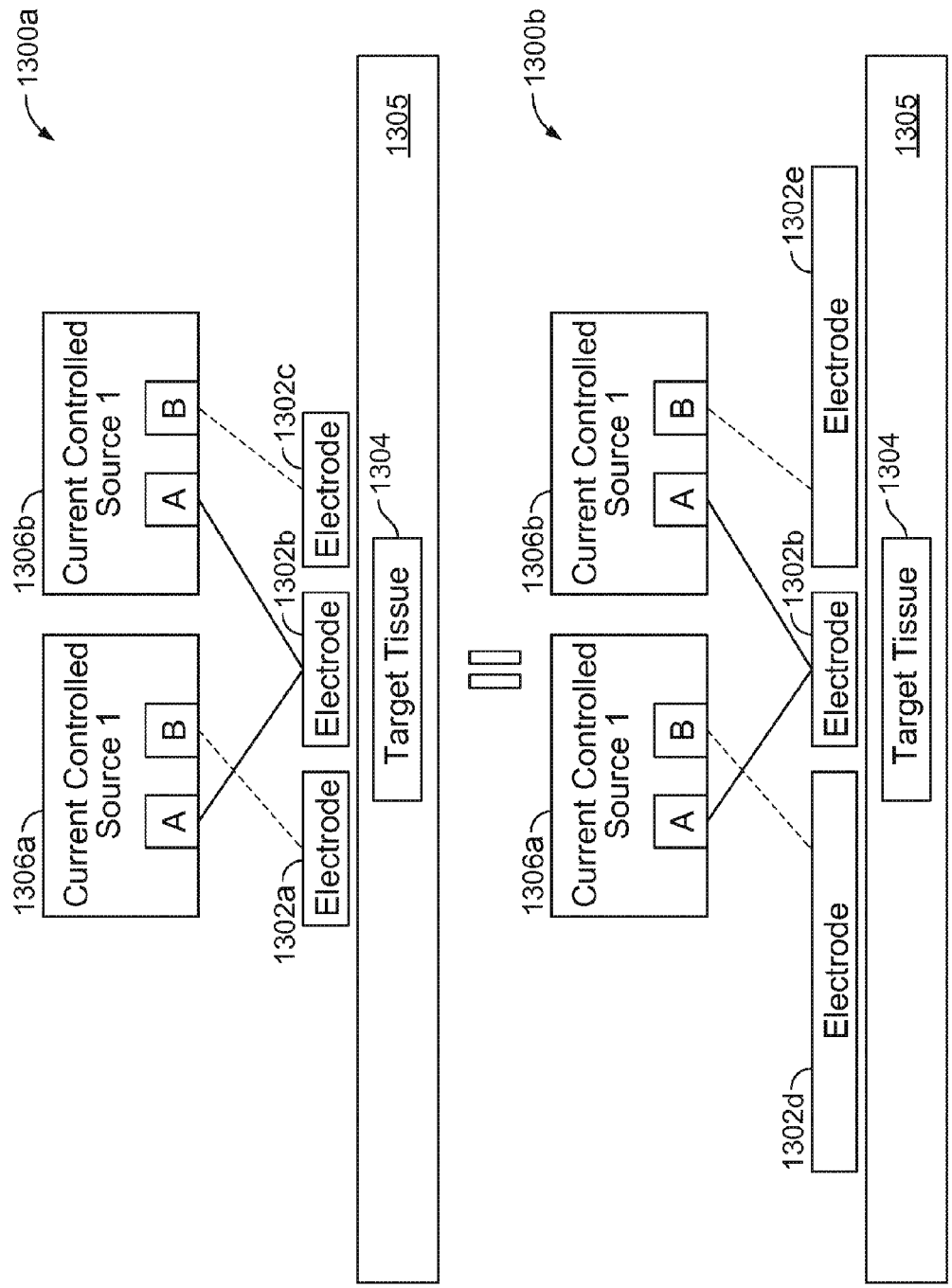

FIG. 13 shows schematic representations of two exemplary substantially equivalent neurocranial electrical stimulation systems.

The illustrated systems are substantially equivalent because as long as the total amount of current delivered to the patient in each system is substantially the same, then the therapeutic effect of delivering that current will be substantially the same.

Each system 1300a, 1300b includes a pair of constant current sources 1306a, 1306b, each with a pair of terminals (designated A and B).

In system 1300a, the constant current sources 1306a, 1306b are adapted to deliver current to a target tissue 1304 in a patient 1305 through electrodes 1302a, 1302b, 1302c attached to the patient's skin. In this system 1300a, the "A" terminals of both constant current source 1306a, 1306b are coupled to middle electrode 1302b, whereas the "B" terminal of each constant current source 1306a, 1306b is coupled to a respective one of the outer electrodes 1302a, 1302c.

In the second system 1300b, the outer two electrodes are replaced by larger electrodes 1302d, 1302e.

Changing the size of an electrode in a system generally does not substantially impact the therapeutic effect that the system can produce as long as the same amount of current can be delivered to the patient.

Figure 14:
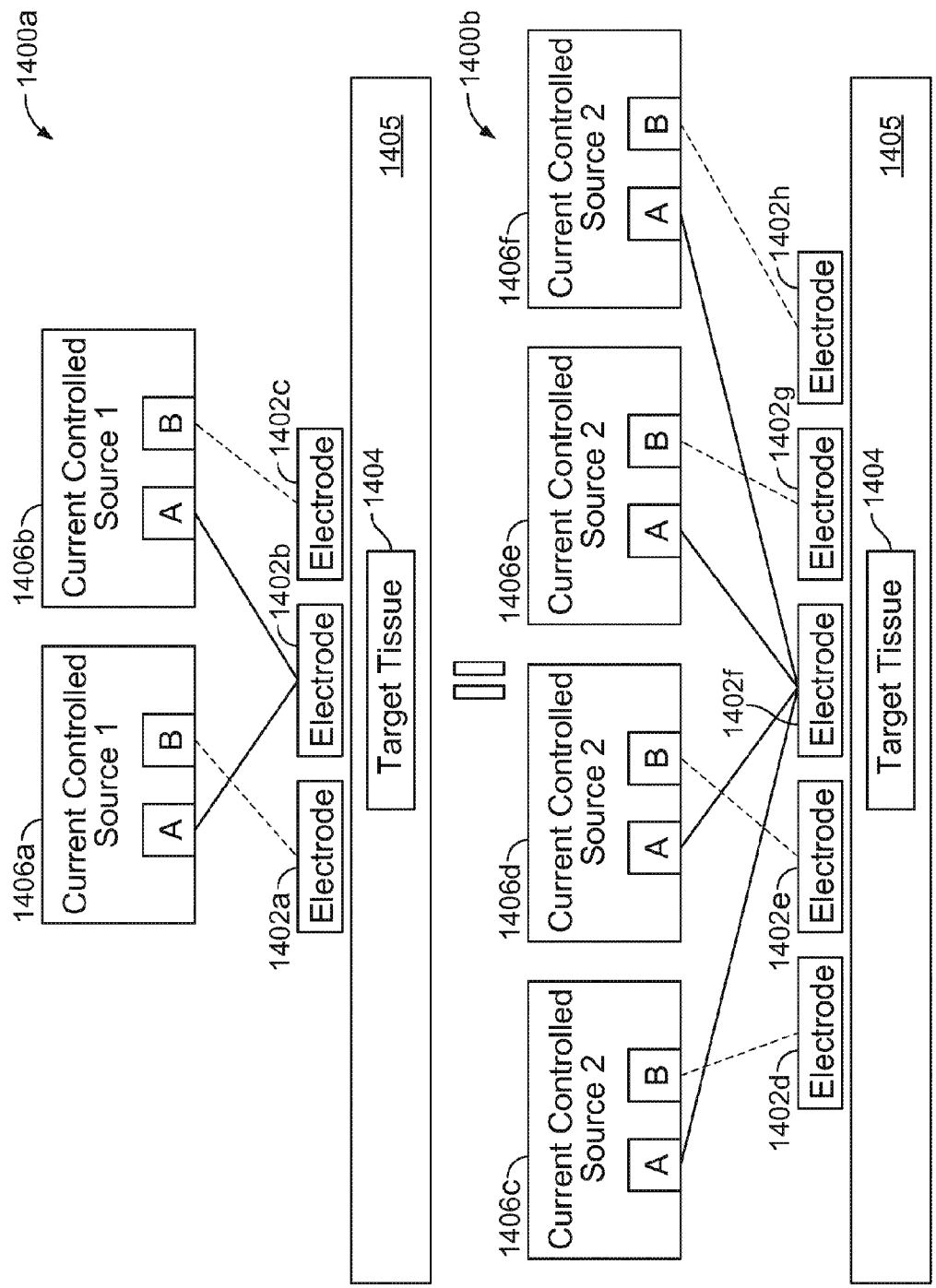

FIG. 14 shows schematic representations of two exemplary substantially equivalent neurocranial electrical stimulation systems.

The illustrated systems are substantially equivalent because as long as the total amount of current delivered to the patient in each system is substantially the same, then the therapeutic effect of delivering that current will be substantially the same.

Each system includes constant current sources, each having a pair of terminals (designated A and B) adapted to deliver electrical current to a target tissue 1404 in a patient 1405 through electrodes attached to the patient's skin.

The system 1400a has fewer constant current sources and fewer electrodes than the system 1400b. More particularly, system 1400a has two constant current sources 1406a, 1406b and three electrodes 1402a, 1402b, 1402c, whereas system 1400b has four constant current sources 1406c-1406f and five electrodes 1402d-1402h.

In order to produce substantially the same therapeutic effect in each system 1400a, 1400b, substantially the same amount of current is delivered by each system to the patient. Thus, each constant current source and electrode in the system 1400b produces and carries less current than each constant current source and electrode in system 1400a. Carrying less current per electrode can sometimes reduce the incidents of burning in a patient.

In some implementations, an equivalent electrode configuration exists between a pair of electrodes that are spaced apart from one another and a single electrode between where the pair of electrodes were placed. In some implementations, the single electrode is larger than the two separated electrodes that were replaced. Similarly, in some instances, it is possible to produce a substantially identical therapeutic effect by passing current through a single electrode placed directly over a target tissue as compared to passing current through two or more electrodes that are not placed directly over the target tissue. In such instances, the amount of current that passes through the single electrode placed directly over the target tissue typically is greater than the amount of current that passes through each of the two or more electrodes not placed directly over the target tissue. However, the amount of current that passes through the single electrode placed directly over the target tissue typically is less than the total amount of current that passes through each of the two or more electrodes being replaced. In some implementations, it is possible to produce a substantially identical therapeutic effect in a system if the amount of current being passed through one or more of a plurality of electrodes is changed, but the total current being delivered is unchanged.

Figure 15:
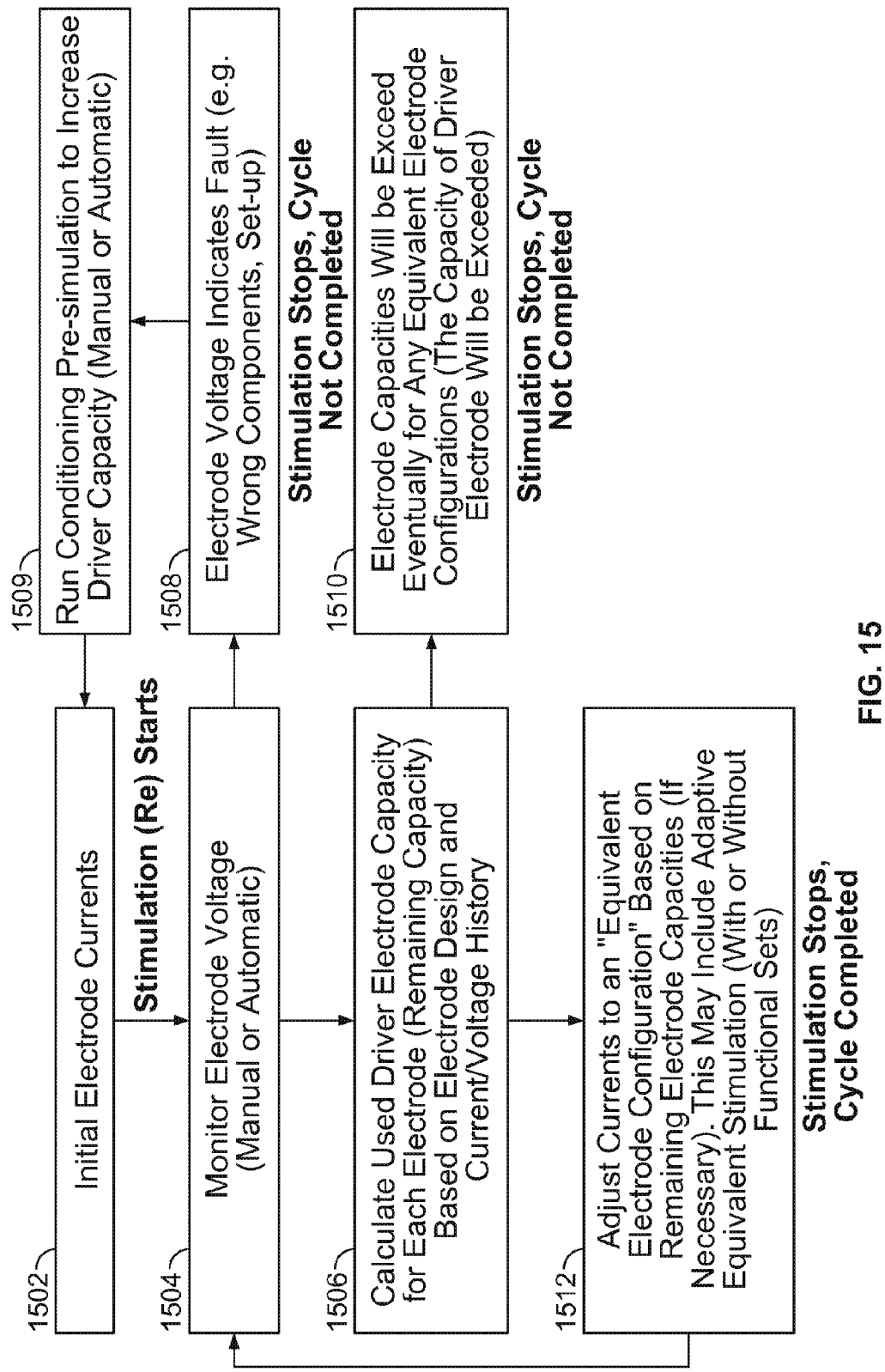
FIG. 15 is a flowchart of a method of adjusting current flows in a neurocranial electrical stimulation system.

FIG. 15 is a flowchart showing an exemplary implementation of technique, that can be implemented automatically or manually, for an adaptively shifting current around between electrodes in a system in a manner that will produce a substantially identical effect from a therapeutic effect.

The illustrated technique involves delivering 1502 initial electrode currents to a patient, enabling stimulation to start or restart.

The technique involves monitoring 1504, either manually or automatically, electrode voltage.

If the monitoring indicates a fault 1508, the stimulation stops although the treatment cycle has not been completed. The method then includes running 1509 conditioning pre-stimulation to increase the DRIVER capacity, either manually or automatically. Subsequently, stimulation restarts at 1502.

The technique also involves calculating 1506 used DRIVER electrode capacity for each electrode (remaining capacity) based on electrode design and current/voltage history. If electrode capacities will be exceeded eventually for any equivalent electrode configurations 1510, then stimulation stops although the treatment cycle has not been completed.

Alternatively, the method includes adjusting 1512 currents to an equivalent electrode configuration based on the remaining electrode capacities (if necessary). This may include adaptive equivalent stimulation, as discussed herein, with or without functional sets. After currents are adjusted, monitoring electrode voltage continues 1504.

Once the treatment cycle is complete, the stimulation stops.

In some implementations, electrodes are secured to a patient's head with a first set of one or more electrodes ("active" electrodes) that deliver and/or return therapeutic current to/from areas of the patient's head to treat a target tissue, and a second set of one or more electrodes ("idle" electrodes) that do not deliver or return current to the patient's head, but are secured to the patient's head. An example of such a system is shown in FIG. 16 which shows five schematic representations of electrodes (represented, for example, by dots) secured to a patient's head.

In some implementations, when a therapeutic amount of current is passed through the active electrode(s), one or more of the idle electrodes detect a voltage at the patient's skin. The amount of voltage detected at each idle electrode is generally a function of the idle electrode's proximity on the patient's head to one or more of the active electrodes, the current being passed through the active electrode(s), the current's conductive path through the patient, the idle electrode's proximity to the conductive path and other factors. In general, the closer an idle electrode is to an active electrode that is passing current and the more current that is being passed, the larger the voltage will be that the idle electrode senses.

In a system that includes active electrodes and one or more idle (or passive) electrodes, the amount of voltage that each passive electrode should sense when a particular current is passed through the active electrodes can be estimated. The estimated amounts of voltage expected to be detected by each idle electrode is then compared to the actual voltages detected at each idle electrode during system operation to determine if the system is operating as expected.

If the actual voltages detected at each of the idle electrodes are not sufficiently close to the estimated voltages, this could indicate a problem with the system (e.g., a current source or an electrode is not delivering current as expected). In some implementations, the occurrence of such problems, causes the system to provide an indication to the system operator (e.g., an alarm) that a problem exists. The system operator could then opt to take corrective action. In other implementations, the system is adapted to automatically shift current around (e.g., from a faulty active electrode to one or more good active electrodes) to produce a substantially identical therapeutic effect as the originally expected current delivery scheme.

In some implementations, the foregoing technique is used as an initial test to confirm that the active electrodes are placed correctly and are capable of passing current to the patient in a desired manner. In some implementations, the voltage at the idle electrodes is monitored in a continuous (or at least periodic) manner throughout a treatment procedure to monitor for system problems that may develop during the treatment procedure (e.g. a current source fails).

Each of the five schematics in FIG. 16 illustrates the distribution of voltage across the patient's head under different current delivery schemes. In the illustrated schematics, only a small number of electrodes are "active" (that is, carrying current to and from the patient. The rest of the electrodes are passive, but are capable of detecting, in their respective passive roles the presence of voltage (resulting from the flowing current) at their various positions. Depending on a variety of factors, the voltages sensed can be used to automatically detect is there is a system problem or if a desired energy distribution in the patient's head is being achieved. In the figures the area of maximum voltage on the scalp is illustrated by a darker filled in region while the lines represent iso-potential (single voltage) lines on the scalp. Both the peak and the profile of scalp voltage detected by idle electrodes can be used to distinguish between electrode configurations and also between desired and faulty application of specific electrode configurations. In one embodiment, the rationale outline herein for the control of current during stimulation is similarly applied in this scalp-voltage validation process, as it is important to control the current applied to the cranium for this validation process to be most accurate.

Figure 17A:
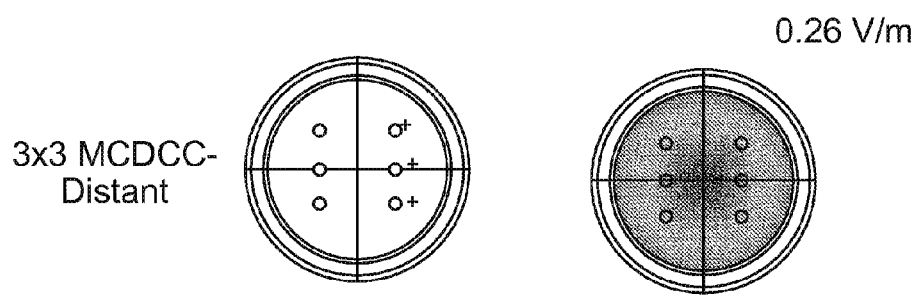
FIGS. 17A and 17B show distribution of electric field strength in a patient's head with different electrode configurations.
Figure 17B:
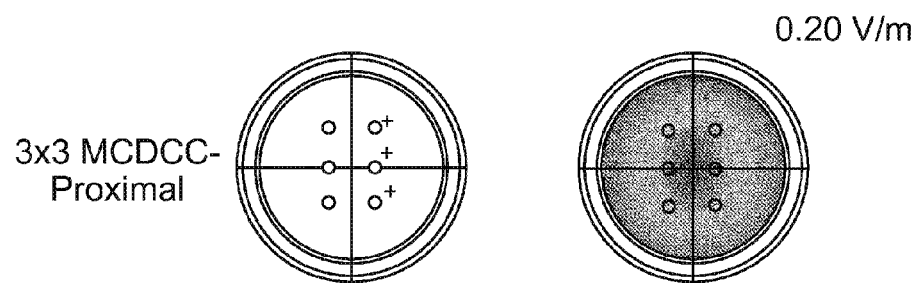

The distribution of electric field strength and, therefore, the voltage that should be sensed by the idle electrode(s) is predictable. FIGS. 17A and 17B, for example, include computer models of a patient's head showing distribution of electric field strength (V/m) across the patient's head with different electrode configurations. However, either one of these configuration may be advantageous for other regions for example limited current loss across the scalp, sensation, and compactness.

The electrode configuration in FIG. 17A has two substantially parallel strips of electrodes (each electrode is represented as a small circle in the figure), the electrodes in one strip having an opposite polarity as the electrodes in the other strip. The dark area between the strips of electrodes represents electric field strength, with darker areas (near the center) representing stronger electric fields. The peak electric field strength in the illustrated model is 0.26 V/m.

The electrode configuration in FIG. 17B also has two substantially parallel strips of electrodes (each electrode is represented as a small circle in the figure), the electrodes in one strip having an opposite polarity as the electrodes in the other strip. The strips of electrodes in FIG. 17B, however, are closer to one another than the strips of electrodes in FIG. 17A. As in FIG. 17A, the dark area between the strips of electrodes in FIG. 17B represents electric field strength, with darker areas (near the center) representing stronger electric fields. The peak electric field strength in the illustrated model is 0.20 V/m.

It can be seen that, although the electrode configurations are different in FIGS. 17A and 17B, the patterns of electric field strength produced by passing current through the electrodes are substantially similar. More particularly, the electric field is substantially contained to the area between the two strips of electrodes, with the electric field strength gradually moving toward the middle of the space between the electrodes.

In a typical implementation, the electric field strength at any spot in the brain (and the intensity of brain modulation in that spot) is proportional to the amount of current flow in or around each area of the brain.

Figure 18:
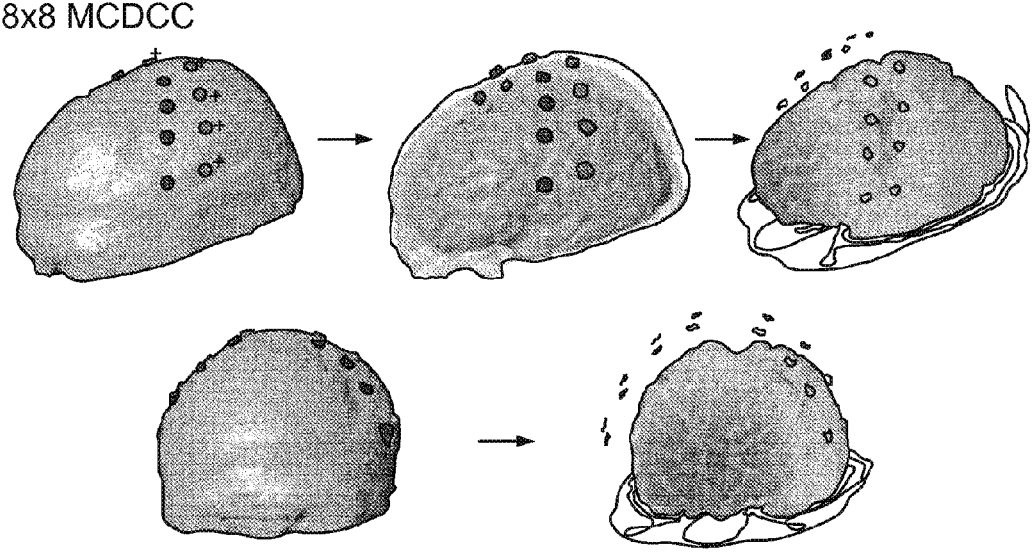
FIG. 18 shows distribution of electric field strength in a patient's head with an electrode configuration.

The distribution of electric field strength in a patient's head can be approximated for virtually any electrode configuration. FIG. 18, for example, includes drawings of and computer models of a patient's brain receiving neurocranial stimulation from two substantially parallel strips of eight electrodes each (each electrode is represented as a small circle in the figure), the electrodes in one strip having an opposite polarity as the electrodes in the other strip. Each strip crosses over the top of the patient's head.

The model shows a darkened band on the brain between the two strips of electrodes. The darkened band represents the distribution of electric field strength in this area. It can be seen that the electric field produced by the passage of current through the electrodes is substantially contained in the space between the strips. The darkened areas at the front and back of the brain models shown in FIG. 18 are not intended to represent electric field strength in these areas.

Figure 19:
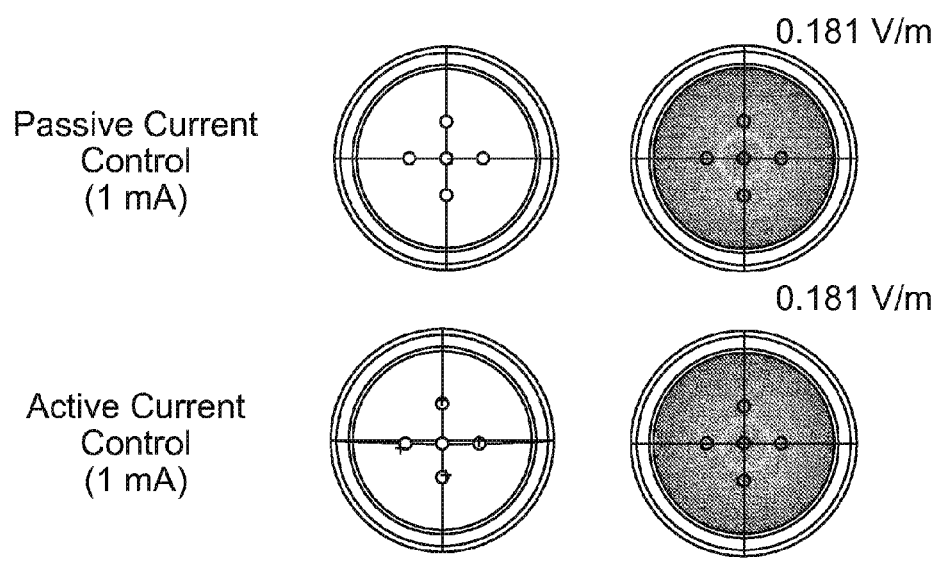
FIG. 19 shows distribution of electric field strength in a patient's head using active and passive control.

FIG. 19 includes computer models of a patient's brain receiving neurocranial stimulation through an electrode configuration that includes a single inner electrode of a first polarity substantially surrounded by four peripheral electrodes of second opposite polarity.

In FIG. 19 (top), all four peripheral electrodes are connected to one terminal of a constant current source and the single inner electrode is connected to the other terminal of the constant current source. Each constant current source has a pair of terminals with opposite polarities. In FIG. 19 (top), the stimulation has been configured as described herein, for example using an adaptor prior to stimulation, such that there is not bad electrode and stimulation delivery to each of the four peripheral electrodes is approximately balanced, for example using intelligent resistance measurement. In this way, and by reference to the following example, it may be understood that safe and effective Neurocranial stimulation may require special measures as outlined herein to operate the system properly. In FIG. 19 (bottom), however, the four peripheral electrodes are connected to four different constant current sources, respectively and the single inner electrode also is connected to the four different constant current sources. Each constant current source has a pair of terminals with opposite polarities.

By comparing the illustrated models, it can be seen that, when the systems are operating properly to pass a therapeutic amount of current through a patient, the distribution of electric field strength is virtually identical. Moreover, in both cases, the peak electric field strength that occurred in response to administering a total current of about 1 mA was the same (i.e., 0.181 V/m).

Therefore, at least in some instances, only if a system is configured properly, there is virtually no difference in the therapeutic effectiveness of actively controlling current at each electrode (e.g., in the constant current system of FIG. 19, bottom) and passively splitting current to multiple electrodes (FIG. 19, top).

If, however, one of the four peripheral electrodes became partially dislodged from the patient, for example, resulting in a large increase in resistance between the partially-dislodged electrode and the patient's skin, the constant current system and the passively dividing system react in very different ways. In the passively dividing system, the increased resistance would cause some or all of the current to shift from the partially-dislodged electrode to the other three electrodes, thereby changing the current flow path through the patient and, at least potentially, changing the therapeutic effectiveness of the current flowing through the patient.

The controlled current system (also sometimes referred to as "active" systems), on the other hand, would react to the partially-dislodged electrode by increasing the voltage to the partially-dislodged electrode to maintain the current being delivered at a relatively constant level. This would maintain the paths that the current follows through the patient and would maintain the therapeutic effectiveness of the current flowing through the patient, despite the partially-dislodged electrode.

FIG. 22 shows computer models of brain activation, specifically tangential oriented regions of the cortex, for the case of Passive Control (good contact), Passive Control (bad contact), Active Control (good contact) and Passive Control (bad contact), illustrating one example as described above. It can be seen that the a bad contact distorts and impairs brain activation for the passive system, but for the active system the bad contact is compensated for leading to unchanged brain activation. In some instances, therefore, the current controlled active system provides superior control, safety, and efficacy again situations where the quality of an electrode is diminished ("bad" electrode) for any reason.

In some implementations, substantially equivalent electrode configurations, from a therapeutic perspective, include one or more electrodes that are positioned at approximately the same positions as one another, but that are different sizes. Similarly, in some implementations, substantially equivalent electrode configurations, from a therapeutic perspective, include a single electrode in one configuration and a pair (or more electrodes) in the other configuration.

Figure 20:
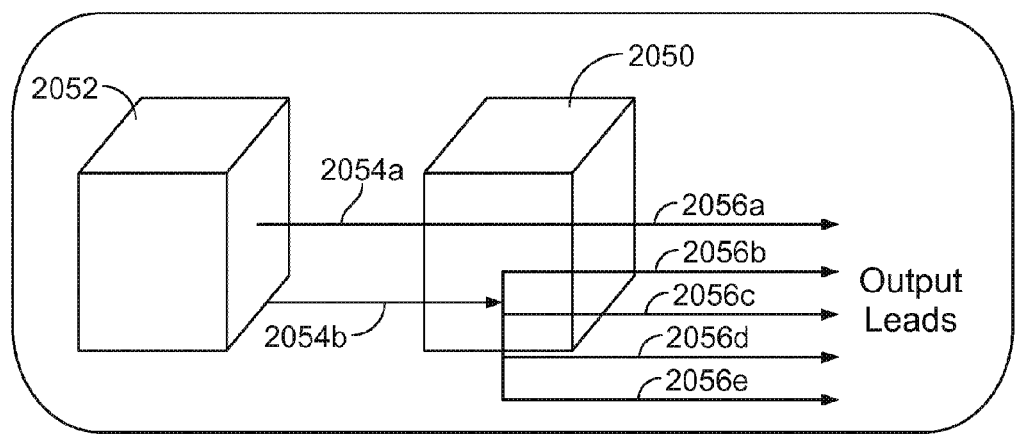
FIG. 20 is a schematic diagram of a passive splitting interface device.

FIG. 20 is a simplified schematic representation of a stimulation interface device 2050 that can be used, for example, to supply current from a single, conventional 2-terminal, constant current source 2052 to a plurality of electrodes.

In a typical implementation, the interface device 2050 has more than one operational mode. The schematic representation in FIG. 20 represents one of those operational modes, which is referred to herein as "pass mode."

The illustrated interface device 2050 has two input terminals 2054a, 2054b and five output terminals 2056a-2056e. In pass mode, one of the input terminals 2054a is directly connected to one of the output terminals 2056a. As such, the current flowing through the input terminal 2054a at any given time will be equal to the current flowing through the output terminal 2056a. Additionally, in pass mode, the interface device's other input terminal 2054b is directly connected to four of the output terminals 2056b-2056e. As such, current flowing into input terminal 2054b is split among the four output terminals 2056b-2056e so that the total current flowing out of the four output terminals 2056b-2056e is equal to the and/or current flowing into the four output terminals 2056b-2056e is combined so that the total current flowing into the four output terminals is equal to the total current flowing out of the input terminal.

In the illustrated implementation, each of the interface device's input terminals 2054a and 2054b is electrically coupled (by wires, for example) to a respective one of the constant current source's terminals 2058a, 2058b. Additionally, each of the interface device's output terminals is electrically coupled to an associated output lead. In a typical implementation, each output leads terminates at an electrode that can be secured to patient's skin.

In some implementations, the interface device 2050 has two other functional modes, referred to herein respectively as scan mode and buffer mode.

In scan mode, the interface device can function as a low-current lead resistance meter, which can provide the operator with information about lead quality and potential faults in the system. In SCAN MODE the maximum output is nominally about 7 μA. In SCAN MODE, a TICKLE features activates a transient <100 μA pulse, intended to regulate lead resistance. When set to SCAN MODE the interface device disconnects the input terminals 2054a-2054b from the output terminals 2056a-2056e.

In some implementations, the interface device is adapted to measure the resistance across each of its terminals (i.e., terminal to terminal). Accordingly, the interface device obtains an indication of the resistance of the external circuit, including the patient, to which it is connected. In some instances, this measured resistance can indicate whether two or more of the electrodes form a functional set. In some implementations, the interface device can provide an indication (e.g., a visual or audible indication) that two or more of the electrodes connected to the interface device form a functional set. This functionality, in some implementations, enables a system operator to confirm the existence of one or more functional sets. In some implementations, the system operator may use this information to confirm that passive splitting is appropriate. In other implementations, the system operator may use the information provided by the interface device operating in scan mode to adjust the position of one or more electrodes to create one or more functional sets.

In buffer mode, the interface device 2050 disconnects its input terminals 2054a from its output terminals 2056a-2056e. In buffer mode, the interface device's output voltage and current is zero.

Figure 21B:
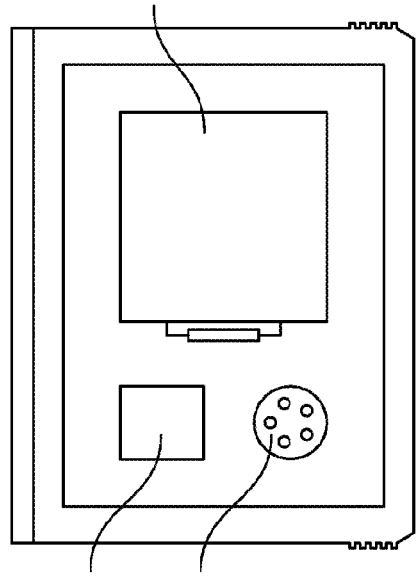
FIGS. 21A and 21B are front and rear views of an implementation of a passive splitting interface device, respectively.
Figure 21A:
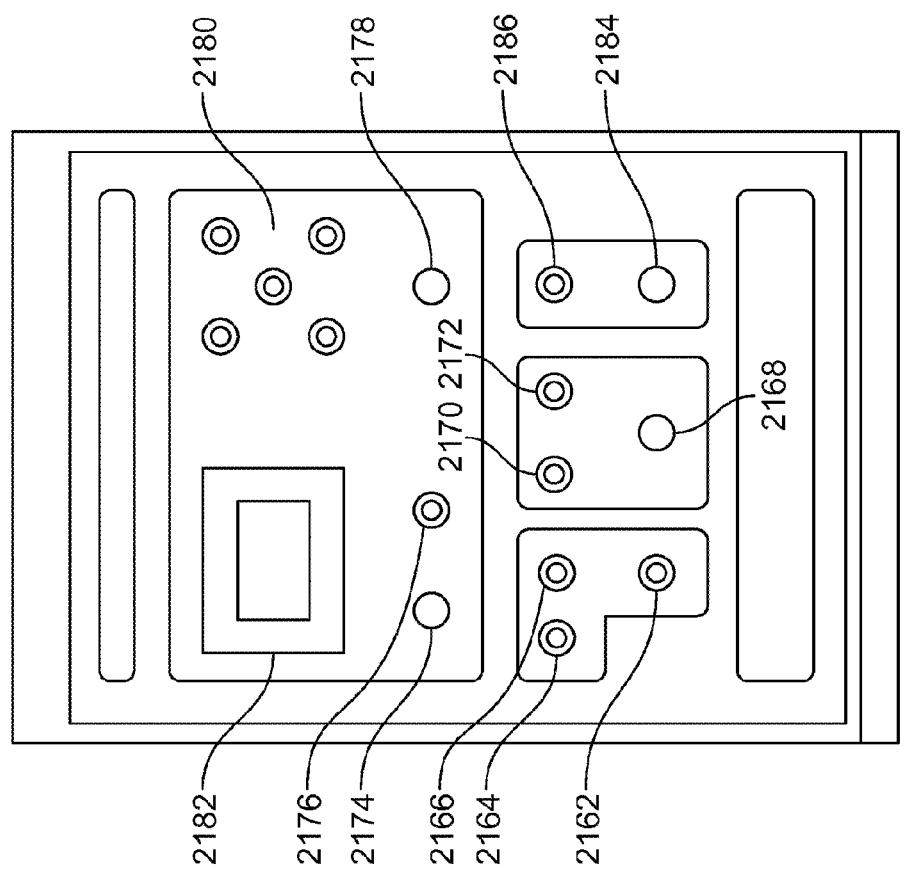

FIGS. 21A and 21B show a front control panel and rear terminal panel of an exemplary embodiment of an interface device 2950.

The illustrated front control panel has a power switch 2162, a low battery indicator 2164, a power on indicator 2166, a MODE selection switch 2168, a scan mode indicator 2170, a pass mode indicator 2172, a prestim tickle switch 2174, a prestim on indicator 2176, a lead toggle switch 2178, a lead indicator 2180, a lead quality display 2182, a buffer mode on switch 2184, a buffer mode indicator 2186, an input receptacle 2188 (with input terminals 2954a, 2954b), an output receptacle 2190 (with output terminals 2956a-2956e) and a battery compartment 2192.

When the interface is operating in scan mode, pressing the prestim tickler button 2174 causes a single electrical conditioning pulse to be passed through the output terminals.

In scan mode, an indication of the quality of each circuit associated with a particular lead is presented at the lead quality screen 2182. The lead toggle button can be pressed to toggle between leads. Each time the lead toggle button is pressed, a next lead is selected for quality assessment. The corresponding lead indicator turns on indicating the selected lead; the selected lead number and color is indicated. The lead quality display provides a value associated with lead quality for the selected lead.

An exemplary interface device has the following specifications:

In Scan Mode
Output Current: nominally <7 µA
Tickle current: <100 µA
Number of channels: 5
Range of measurement: 0-2V
Power Source
Batteries: 2 alkaline 9.0V batteries
Run time: ~8 hrs depending on use
Low Battery Indicator: At 75% of max voltage
Physical Dimensions
Dimensions: 197 mm×155 mm×121 mm
Weight: 2.8 lb
Display: Date1 4 digit LCD
Cables
Input Cable: Shielded 2 channel
Connectors: Split Banana to 3 pin XLR type
Length: 4 Feet
Weight: 0.6 lb.
Output Cable: Shielded 5 channel
Connectors: Circular 5 Pin Standard Din to Din-5 leads
Length: 5 feet
Weight: 0.8 lb
Switches
Mechanical: Push type
Digital: Electronic IC
Emergency stop: Buffer Switch In some implementations, utilizing an interface device as disclosed herein in connection with transcranial stimulation can enhance the system's efficacy and safety.

A number of embodiments of the invention have been described. Nevertheless, it will be understood that various modifications may be made without departing from the spirit and scope of the invention.

For example, in some implementations, functionality can be provided in a system to measure the resistance across two or more circuits that current is being delivered to. This type of system is sometimes referred to herein as an intelligent resistance system. In some embodiments, a problem is detected and the system operator may be notified or corrective measures may be taken, if the electrical resistance that between any two electrodes, that (at any instant) have opposite polarities, in the sense that one is a sink and one is a source, is less than 1 Ohm, 10 Ohm, 100 Ohm, or 1 kOhm. In other embodiments, the ratio of the resistance between one pair of electrodes is compared to the resistance of at least one other pair of electrodes. In some instances, substantially uneven resistance can lead to an undesired level of shunting across the scalp. If the inter-electrode resistance is less than a predetermined threshold, and if the electrodes are of the same polarity, then in one example the electrodes may be considered as equivalent to one electrode or a functional set. This further control can, in some implementations, improve efficacy and safety. When electrodes have very low resistance between then, for example as a result of being placed next to each-other, and have opposite polarities, then current will enter at one electrode, travel through a gel and/or scalp, and enter the other electrodes without significantly crossing in the brain. This can be undesirable because the scalp/gel shunted current may cause skin irritation or pain, but will not be useful from a therapeutic perspective.

There are a range of techniques that can be used to increase and maximize resistance between electrodes that have opposite polarities at any given instant. For example, one could evaluate resistance before beginning stimulation or monitor resistance during the entire duration of stimulation. In some implementations, independent monitoring of each electrode resistance during stimulation is implemented. More specifically, in some implementations, it is the relative resistance (ratio) of a general current path between electrodes going only through the scalp and the general current path between electrodes going through the brain that should be greater than a minimum value—this ratio excludes the metal and gel resistance since that is common to both paths.

In some embodiments, the intelligent resistance system can use one frequency ranging from DC (0 Hz) to 100 Hz (maintained in the linear range as shown below). In one example, to overcome or correct for the electrode resistance the system measures electrode impendence over a frequency range. In a typical implementation, consideration of resistance between multiple electrodes, electrode polarity, and resistance ratios together can provide a system for safe and effective neurocranial stimulation. In addition, this intelligent resistance measurement system, in some implementations, is integrated with a stimulation system. One example that shows, but does not limit, this integration concept is the use of SCAN mode in the interface device disclosed herein.

Electrodes can be configured in a variety of ways. For example, electrodes may be arranged in a strip like fashion to target specific anatomical structures. In some implementations, three sets of electrodes form three strips where the polarity of the middle strip is opposite the polarity of the outer strips. For example, a 6×6×6 configuration can, in some instances, be optimized to target an elongated section of the cortex. Additionally, such a configuration can be used to target gyri. Another configuration includes one or a plurality of electrodes of one polarity (inner core) is surrounded by two or more electrodes of the opposite polarity (outer ring). For example, four electrodes of one polarity may surround one electrode of the opposite polarity (4×1). As another example, 6 electrodes may surround 2 electrodes (6×2). As another example, 8 electrodes may surround 4 electrodes (8×4) including for the purpose of targeting a larger region. As another example, the inner core and outer core of electrodes may be arranged in a manner such that the border between these two groups circumscribes a strip, a strip as wide a one cortical gyri, a strip as wide as two cortical gyri, a circle, a square, a region roughly equal to the entire head, or a region roughly equal to half the head, or a region of the eye, or a region of the ear. In another example, two regions are simultaneously created where the cores may have opposite polarities or the same polarities. For the case of cores with the same polarities, a portion of the outer ring electrodes may be shared between the two regions.

Figure 23:
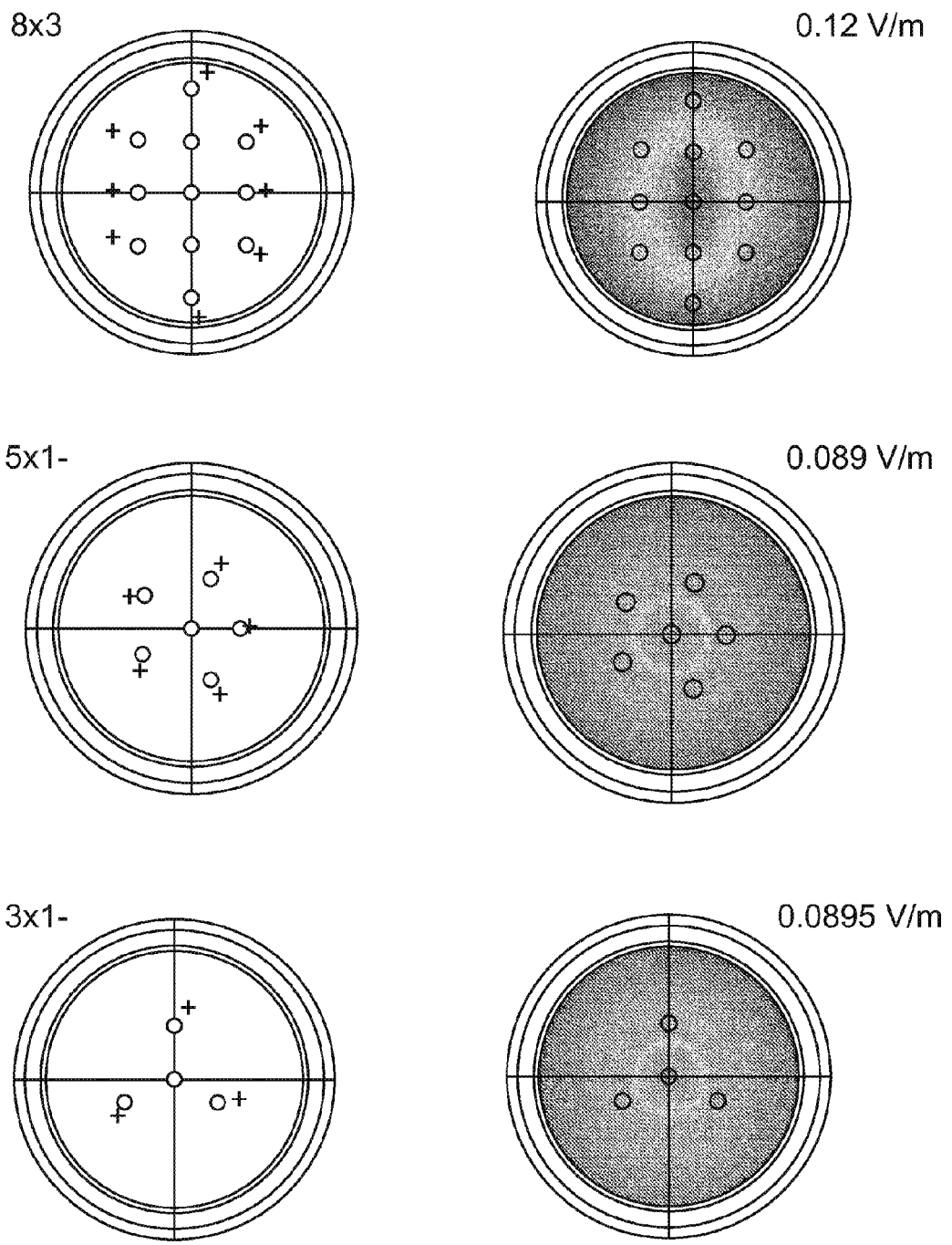
FIG. 23 shows distribution of electric field strength in a patient's head with different electrode configurations.

FIG. 23 shows the electric field in a patient's brain under different electrode configurations. In all cases, the stimulation has been configured as described herein, for example using an adaptor prior to stimulation, such that there is no bad electrode and stimulation delivery to each of the surrounding electrodes is approximately balanced, for example using intelligent resistance measurement. In this way, and by reference to the following example, it may be understood that safe and effective Neurocranial stimulation requires special measures as outlined herein to operate the system properly. In FIG. 23 (TOP) an 8×3 configuration is applied with the 3 inner electrodes arranged in a linear fashion. Combined with the current control system this leads to an approximately uniform strip of activation shown as the inner dark region surrounded by a lighter circle. In FIG. 23 (MIDDLE) a 5×1 configuration is used in combination with the methods of current control described here leading to a circular region of activation indicate by the darker region surrounded by a lighter circle. It can be understood by comparing FIG. 23 (TOP) and FIG. 23 (MIDDLE) that the additional features of 8×3 allow strip versus circular region stimulation. In FIG. 23 (BOTTOM), a 3×1 configuration is used in combination with the methods of current control described in this invention. A region of activation is indicated by the darker region surrounded by the lighter region. In can be understood by comparing FIG. 23 (MIDDLE) and FIG. 23 (BOTTOM) that under specific conditions and using methodology of current control and intelligent resistance measurements, the number of electrodes need to produce activation in a targeted region may be reduced. In some application where there is a desire or need to reduce the number of current sources and/or electrodes the techniques disclosed herein provide means for doing so.

Moreover, the number of electrodes in the inner ring can be less than the number in the outer ring; and the number of current sources connected to the outer and inner electrodes is the same; such that the number of current sources sharing an electrodes in the inner core is higher then the number of current sources sharing an electrodes in the outer core. In some of such implementations, the number of electrodes is two times the number of sources (number of channels) minus 1, or less. In a yet preferred embodiment, the number of inner electrodes is less than or equal to half the number of electrodes in the outer ring. One could also consider the number is inner electrodes is equal to half the number of electrodes in the outer ring, or less. In some instances, the number of electrodes is equal to two times the number of sources (number of channels) minus half the number of electrodes in the core of less, or the number of electrodes is equal to two times the number of sources (number of channels) minus half the difference in number of electrodes between the outer and inner core, or less. Thus the number of current sources needed can be reduced based on the difference in the number of electrodes between the outer ring and inner core, where reducing the number of current sources is advantageous. Using the methods described herein, the number of current sources (or current channels) can be reduced to the number of electrodes in the outer ring.

In some implementations, the distance between the inner and outer electrodes of controlled and the inner electrodes are positioned over the target. In another embodiment, the outer ring circumscribes the target. In another embodiment, the middle space between the inner and outer ring circumscribes the target.

In another embodiment, a method includes defining a target region, where the target region may be a region of the cortex, and the region may be defined as a two dimensional surface of the cortex, and then trans-projecting that target to the skin surface. The method of projection can be a mathematical function whose parameters may include a generic or individual anatomy, generic of individual tissue properties such as resistivity, and other modeling techniques that include, for example, activating functions, finite element methods, and laplacian theory. For example the method or projection may be largely radial where the cortical surface is projected to the skin in a direction radial to the skin surface or radial from the brain center. In another example, the method of projection may be surface convoluted where the projection from each region is based on generic of individual cortical folds. In this way, the projection for a non-convoluted region of cortex will be different from a convoluted region of cortex. In this way, the gyri and sulci are part of the projection method. In the second step, a plurality of electrodes is positioned on the cortex based on this projection. For example, a plurality of electrodes may be placed on the cortex and current passed through these electrodes in a manner than an ispotential line on the skin surface corresponds to an aspect of the trans-projection on the skin surface. One application of this is to position electrodes to surround trans-projections.

In one application, the following steps are taken:
I. Two or more pairs (for example four pairs) of current sources are provided. Each current source has two terminals (A and B for each current source). It is ensured that (in any instant) the polarity of all the A's and all the B's is the same (for the DC case the A is only anodes and B is only cathodes; but for AC they switch together). The current magnitudes at the A and B across independent current sources can match (e.g. 1 mA everywhere) or may not. In one example, one current source can be 1 mA and another can be 0.5 mA. Of course within each current source A and B always match and of course are exactly opposite for that current source.
II. Position all the A's so they form the "inner core" and position all the B's so they form the "outer ring". For example, 4 A anodes on the inside, and 4 B cathodes forming a ring around this. For example a 4×4 Ring Design. The B's are around the target region.
III. The A's on the inside can share electrodes (but not the B's on the outside). For example, if 4 A's share one electrode then, generally, the current the A's deliver is "pooled" into one central cluster. For example, A with 1 mA and another A with 0 mA or they both have 0.5 mA. Only the total is regulated in this case.

In another embodiment, the number of Neurocranial (DRIVER) functional electrode sets is equal to two times the number of current controlled sources (number of channels), minus the number of channels that share a electrode functional set, plus the number of electrode functional sets with more than one current channel connected to them. This embodiment is highly advantageous form the perspective of efficacy and safety as it allows control of the current delivered to each electrodes and precludes passive splitting of current from one current channel to two ore more electrode functional sets (where desired).

In a system that includes, for example, four electrodes of one polarity surrounding an electrode of another polarity (4×1), changes in electrode resistance, as may occur for a faulty electrode, affect the resulting brain modulation for the case of passive current control in the four surround electrodes, and full current control at all electrodes are different. Shift of tangential currents and loss of undirectionality may occur when passive current control is used with one faulty (bad) contact.

In some implementations, knowledge of skin condition (e.g., induced skin voltages) may be used to help predict brain modulation.

In some embodiments, the main power of stimulation (main power frequency band) is limited to frequencies less than 100 Hz. For example more than 50% or 90% of the power is below 100 Hz. In some embodiments, the stimulation intensity is less than 1 mA or less than 4 mA or less than 10 mA. In some embodiments, the stimulation intensity is less than 1 mA per square centimeter or 4 mA per square centimeter or 10 mA per square centimeter.

In some implementations, an intelligent resistance system is used to identify a functional set or may be use to validate a functional set. For example in SCAN mode prior to stimulation. This may include monitoring voltage across a functional set or across each electrode within the functional set. Typically, electrodes within the functional set are inherently the same polarity.

In some embodiments, four electrodes are arranged in a square array such that they form a functional set. In this way, all four electrodes can be connected to once current channel or line, and the distribution of current within the functional set will not effect brain modulation. This could be a passive functional set. Alternatively, the electrodes can each be connected to an independently controllable current source or line, such that the total current to the array is set by the sum of the current from these lines. This could be a fully active functional electrode set. Adaptive electrical stimulation may be used in this case where the total current sum is maintained at a desired value, but the current is split between the four electrodes in a manner that minimizes electrode potential at one of more of these four electrodes. In one embodiment, the resistance between each of the electrodes is monitored.

In another embodiment, during stimulation, the current supplied by one or more sources is adjusted in a manner such the initial and final currents result in what is referred to herein as Equivalent Electrode Configuration Stimulation. In some implementations, adjustments made pursuant to Equivalent Electrode Configuration Stimulation can be derived from or based on the same or similar techniques as those disclosed herein related to determining equivalent electrode configurations. In a typical embodiment, the current flowing through an electrode is adjusted to maintain the voltage at one of more of the electrodes below a specific threshold.

In general, Equivalent Electrical Configuration Stimulation (also called Equivalent Electrode Stimulation or Equivalent Configuration Stimulation) can, in some instances, increase the efficacy and safety of neurocranial stimulation. Two or more neurocranial electrode configurations may be equivalent electrical configurations as discussed herein. There are distinct configurations of current sources and electrode arrays connected to said current sources that results in functionally equivalent modulation of brain function, or near equivalent modulation of brain function. As such, from the perspective of brain modulation and some aspects neurocranial stimulation outcome, one or more different configurations may be equivalent. However, these configurations are not identical in how they are set-up on the surface of the body and hence one of these configurations may be advantages relative to another configuration. Thus, in some instances, prior to stimulation (e.g., during set-up), or during stimulation, different equivalent electrode configurations may be used, where switching between the different equivalent electrode configurations does not change relevant aspects of brain modulation but one may be preferable for conditions on the surface of the body.

Substantially equivalent configurations in Equivalent Electrode Configuration Stimulation do not need to have the same number of stimulation sources or the same number of electrodes, or electrode positions, or the same electrode geometry. In fact, it is this flexibility that makes Equivalent Electrode Configuration Stimulation particularly useful and effective for neurocranial stimulation. The special case where two Equivalent Electrode Configuration Stimulations have the same number of electrodes, with the same shape, and in the same position may be referred to herein as Fixed Position Equivalent Electrode Configuration Stimulation. Two Fixed Position Equivalent Electrode Configuration Stimulations generally differ only the amount of current that is provided to each individual electrodes. Some examples of Fixed Position Equivalent Electrode Configuration Stimulation used functional sets of electrodes.

In one embodiment, the number of electrodes used for neurocranial stimulation can be reduced by applying equivalent electrode configuration techniques, disclosed herein. The use of a minimum number of electrodes used for an application can, in some instances, be highly advantageous in improving the simplicity and robustness of a system. In one embodiment, the equivalent electrode configuration requiring the least number of electrodes is used.

In another embodiment, the number of electrodes needed for neurocranial stimulation is reduced to the minimum number needed plus a number of redundant electrodes, where the redundant electrodes are used to add robustness to the system. For example, if one electrode fails, then the redundant electrode can activate. A single device is able to stimulate in two or more configurations. In some such systems, the stimulator is configured and programmed in a manner to specifically take advantage of this redundancy.

In some implementations, configurations having small and large internal electrodes surrounded by other electrodes are substantially equivalent for purposes of equivalent electrode configuration stimulation. The peak electrode current density is decreased for the large internal electrode configuration. By making the area of the internal electrode four times the area of each on of the four outer electrodes, for example, the current density at the inner electrode is equal to the current density at the outer electrodes.

In some implementations, four outer electrodes surrounding two inner electrodes of opposite polarity (4×2) produce similar brain modulation to four electrodes surrounding one inner electrodes (4×1) such that the 4×1 and 4×2 configurations are substantially equivalent for purposes of Equivalent Electrode Configuration Stimulation. But in the 4×2 configuration there are two electrodes functioning in the inner core which may be advantageous for safety and robustness reasons.

In some implementations, a 4×2 electrode configuration can produce similar brain modulation as current distribution is shifted between the two inner electrodes. For example, a distribution of 1 mA and 0 mA, 0.5 mA and 0.5 mA, and 0.9 mA and 0.1 mA can result in the same brain modulation such that these are all Equivalent Electrode Configuration Stimulation configurations. Because the electrode geometry and position is not changed between these cases they can be considered Fixed Position Equivalent Electrode Configuration Stimulation configurations. Thus, if one inner electrode starts to fail, for example, and the electrode potential at that electrode approached a voltage threshold, current can be (temporarily) shifted to another electrode without effecting brain modulation. Such a controlled shift would be a specific example of Adaptive Electrode Stimulation. Such a shift may, in some instances, be advantageous for safety, efficacy, and robustness reasons.

In some implementations, a system of delivering neurocranial stimulation includes:

1) Three or more current controlled lines, where each line may be connect to one or more current sources or current channels from different current sources, where current in each line can be controlled. In a typical implementation, there is at least one source and one sink line at any instant and the total sink and source currents cancels (e.g. sums to the same magnitude values).
2) A booster or buffer may be included in one or more of the lines.
3) Three or more DRIVER electrodes connected to the current controlled lines, where at any instant each electrode may be a source or a sink, which indicates its polarity.
4) Adjusting the current of one more current lines in a manner that does not significantly alter the desired stimulation outcome, where the desired stimulation outcome may include, but is not limited by, the generation of an electric field in the brain with a specific spatial profile or within a specific range.
5) based on or using information from an intelligent resistive measurement; or
6) where a digital potentiometer is used (to regulate the current supplied); or
7) where a micro-controller is used In some embodiments, the current sources are controlled by a control system. In some such embodiments, the voltage across one or more DRIVER electrodes and/or the voltage generated at one of more current sources is (are) monitored and this information is used by the control system. In a still preferred embodiment, the current is adjusted by the control system such that the initial and final current distributions are substantially equivalent from the perspective of therapeutic efficacy.

In some embodiments, each DRIVER electrode is connected to only one line and the current is adjusted to maintain the voltage of at least one DRIVER electrode under that DRIVER electrode's specific threshold. In this case, the polarity (source or sink) and current intensity of the DRIVER electrode is set by the polarity and current intensity in the corresponding line. In some embodiments, two or more DRIVER electrodes form a functional set and current distribution between DRIVER electrodes in a functional set is adjusted. In this case, the electrodes in the functional set are of the same polarity during the period of time in which the Adaptive Electrical Stimulation functionality adjusts current, and generally the total current delivered to the function set remains the same.

In some embodiments, at least one electrode functional set, made of at least two electrodes, is surrounded by at least two electrodes of the opposite polarity. In this case, an automatic algorithm (in a control system) or manual adjustment by the user (using a range of evaluation techniques), may implement Adaptive Electrical Stimulation so adjust to a Equivalent Electrical Configuration.

In some embodiments, current is adjusted in each line such that the configuration (current distribution) before and after adjustment are substantially equivalent from a therapeutic effectiveness perspective. Note that because electrodes are not being moved or re-sized during adaptive electrical stimulation, in this case, the configuration (current distribution) before and after adjustment are also fixed position equivalent electrical configurations. In some implementations, the current is adjusted to maintain the voltage of at least one DRIVER electrode below an electrode specific voltage. In some cases, the current at a given DRIVER electrode is reduced to zero or a value near zero which still allows monitoring of electrode voltage, for example if the DRIVER electrode recovers and can be re-activated.

In some embodiments, two or more electrode configurations are identified that will produce a desired outcome, and Adaptive Electrical Stimulation adjusts or selects between these configurations depending on a cost function relating to DRIVER electrode capabilities. For example, there may be two distinct targets in the brain where either one can be stimulated to achieve the desired outcome. As another example, there may be distinct electrode configurations, potentially involving distinct sets of electrodes, such that both target a given structure to achieve a desired outcome.

In some embodiments, the subject is allowed to rate their level of discomfort or pain, or provide another form of feedback during stimulation, and Adaptive Electrical Stimulation adjusts stimulation based on this feed-back. In another embodiment, one or more sensors or measurement systems used during electrical stimulation, and information from the sensor system is used by the Adaptive Electrical Stimulation control system. In some embodiments, the biological signal is an electrical surface potential such as an EEG or EKG. In another embodiment, Adaptive Electrical Stimulation is adjusted to change the amplitude of the surface bio-potential signal in a specific frequency band.

In some embodiments, the stimulation is maintained in a linear or near-linear range.

In some embodiment, Adaptive Electrical Stimulation, including in cases with a control system, involves determining information about the DRIVER electrodes in a manner that allows separation of the contribution from the tissue. For example, measuring resistance between any two electrodes provides a resistance of the total current path which includes electrodes, the electrode-interface, and all the tissue in-between, while a useful measurements would relate only to a single driver electrode. In some embodiments, the resistance of each electrode is measured against the resistance of one or more of the other electrodes in parallel, thereby diminishing the contribution of the other electrodes and the tissue. In another embodiment, the resistance of each electrode pair is measured serially and the resistance of each electrode is then calculated. In another embodiment, the voltage at each current source is used to determine the voltage expected across each single electrode. In still another embodiment, this is done considering the voltages generated on the scalp by stimulation.

Adaptive Electrical Stimulation can be implemented intermittently, constantly, or when triggered by an operator who has, for example, evaluated the voltage at one or more (and potentially all) the Driver Electrodes. In some instances, a control system collects the information on the electrode voltage, including both current voltage and previous voltage(s), and based on this information, identifies the potential for a DRIVER electrode to exceed its capacity, which can include but it not limited to a electrode voltage. One aspect of evaluating DRIVER electrode capability is a cost function. For multiple electrodes, a cost function is applied to all DRIVER electrodes of interest. The control system, if desired, then calculates a new current distribution in the system that is preventative in regards to DRIVER electrode capacity but minimizes any disruption of stimulation efficacy, for example by switching to a Equivalent Electrical Configuration and/or adjusting current between functional sets.

In some embodiments, a method includes:
1) Selecting a number of electrodes, for example, greater than 3, 4, 10, or 20.
2) Selecting the positions of the electrodes on the body, where, for example, greater than 1, 2, or 20 electrodes are on the scalp.
3) Selecting the current over time at to each electrode SUCH THAT
   a) At any instant, the total current profile (at any given point in time) can be represented mathematically as an equivalent summation of dipoles, where each dipole consists of a magnitude matched sink source pair, where each pole of the dipole it located at the location of one electrode (or functional set); and
   b) At any instant, the number of dipoles is equal to the one half the number of electrodes minus the number of dipoles that share an electrode location plus the number of electrodes associated with more than one dipole; and
   c) The total current over time at each electrode does not exceed as threshold value specified by a mathematical function of the current.

In some embodiments, the current over time is selected such that no pole of any dipole changes location (electrode), but the magnitude of each dipole may change. In another embodiment, each dipole is separated by greater than 1 cm, 4 cm, or 10 cm. In another embodiment, the total current over time is limited in peak amperes. In another embodiment, the total current over time is limited in by total charge. In another embodiment, the total current over time is limited by the integral of current or total assumed unrecovered charges. In another embodiment, the total current over time is by a weighted function of each of the above restrictions.

In yet another implementation, a portable self-contained device is provided for safe and effective neurocranial stimulation that includes:
1) A circuit with multiple electrical sources (e.g., >2, >3, >4) (that is outside the body);
2) DRIVER electrodes and means to position at least one DRIVER electrode on the scalp or cranium, where the number of electrodes (and/or functional sets) is equal to or less than the number of electrical sources.
3) A cable, switches [e.g., multiplexer, de-multiplexer] or circuit, or other electrical means of connecting the electrical sources with the DRIVER electrodes (and/or functional sets) in such a manner that each electrical sources is connected to only one DRIVER electrode (or functional set) at any given time.
4) (In some cases) with one power source (for the stimulation sources) with power regulation as necessary.

In some embodiments, the electrical sources are current sources. In some embodiments, the circuit, DRIVER electrodes, and means of connection are configured such that the current at each electrode can be independently controlled. In some embodiments, the peak current or current over time or integral of the current over time is limited based on the DRIVER electrode capacity. In another embodiment, the voltage generated by each electrical source is monitored by the control system and used to regulate the current supplied to one or more DRIVER electrodes.

In some embodiments, the device is a therapeutic electrostimulation apparatus which operate to supply electrostimulation to the body. In some embodiments, the electrical channels provide the same waveform of signal to the body. In some embodiments, the waveform is a DC waveform, for example, 0.1 to 20 mA in at least one channel applied for 0.1 seconds to 10 days. In another example the DC waveform is 0.2 mA to 10 mA in at least one channel applied for 30 seconds to 10 hours. In another example the DC waveform is about 2 mA in at least one channel applied for 20 minutes. In another still preferred embodiment the waveform is AC or sinusoidal. For example the AC waveform in at least one channel may be 0.1 to 20 mA, with a frequency of 0.001 Hz to 100 MHz applied for 0.1 seconds to 10 days. In another example, the AC waveform in at least one channel may be 0.5 to 5 mA, with a frequency of 1 Hz to 50 Hz applied for 30 seconds to 10 hours. In another example, the AC waveform in at least one channel may be about 2 mA, with a frequency 10 Hz applied for 30 minutes.

The regimens, protocols, and/or waveform applications may be repeats daily over the course of several days, for example over 10 days, or may be repeated within a day, for example several times in one day.

In another embodiment, the current sources are divided into two groups such that one group always generates current of the same polarity; while the current sources in remaining group always generate current of the opposite polarity. In some embodiments, the output of the current sources is DC current for greater than 1 minute, 2 minutes, 10 minutes, 20 minutes, or 60 minutes. In some embodiments, the output of the current sources is DC current is <1 mA, <2 mA, <5 mA, or <10 mA. In some embodiments, one group consistent of less than 5 sources, less than 3 sources or only one source. In some embodiments, one group consistent of 3, 4, 5, or greater than 10 sources more than the other group. In some embodiments, one group consistent of one channel while the other group consistent of four channels. In some embodiments, one group consists of 2 channels while the other group consistent of 6 channels. In some embodiments, the system if configures such that the electrodes connected to one group are surrounded by electrodes connected to the other group.

In another embodiment, user adjustable switches, dials, or other interfaces allow the user to set or program the electrical output of the circuit. In some embodiments, a graphic user interface (GUI) is used.

In some embodiments, displays, lights, and/or other indicators provide information to the user about the operation of the circuit. In some embodiments, a graphic user interface (GUI) is used.

In some embodiments, a function generator is used to generate a waveform which is converted to a current waveform but a voltage-to-current converter. In some embodiments, the current is controlled by a variable potentiometer in the current controlled source. In some embodiments, when the voltage of at least one current source exceeds a threshold, stimulation is aborted or stimulation intensity is decreased.

In some embodiments, a mechanical mechanism is used, where at least a portion of the leads or connective cables is positioned to contour to the shape of the scalp or are otherwise embedded or connected to a head-gear such that the protrusion of the leads or connective cable from the scalp is reduced. In another embodiment, a mechanical mechanism is used, where the positions of the electrodes relative to each other is fixed.

The techniques and systems, in some implementations, can help adapt single current sources supply current to multiple electrodes or to customize their function to individual needs. Electrodes can be interchanged, reconfigured, or otherwise modified without needing to connect/disconnecting cables, etc.—a process that can be burdensome, that introduces additional complexity, and gives rise to the possibility of error. The result is an improvement in safety and efficacy.

In another embodiment, an output waveform is controlled through a user interface. Regardless of waveform, the stimulation configuration and electronics generally are designed to provide multi-channel stimulation.

In a typical implementation, electrodes are rated to stimulation specification and stimulation is applied in such a manner that the rating for any electrode is not exceeded. In some embodiments, current sources are used for neurocranial stimulation and current output is limited. In some implementations, the current delivered to each electrode is regulated not to exceed the electrode specifications. In another embodiment, the current delivered to each electrode is monitored. In another embodiment, the current delivered to each electrode is limited based on a control system.

In a typical implementation, the contact area between electrode gel and the scalp is roughly spherical and less than about 1 cm2, 5 cm2, or 10 cm2.

In some implementations, DRIVER electrode positioning takes into account 1) a head injury or trauma including a skull defect or stroke; and/or 2) where the position is based on some anatomical landmark or feature (e.g. ears, nose, eyes, 10/20 EEG system) and/or 3) analytical (e.g. simple rules) or computational techniques (e.g. FEM) and/or 4) techniques consider "direction of modulation" namely "radial" and "tangential" current flow. Moreover, in some implementations, focus is on the cortical surface so radial and tangential is defined relative to the (undulating) cortical surface. In one embodiment, DRIVER electrodes form one or more arrays.

In some implementations, a system includes:
1) One current source, with a current sink and current source outputs at any instant.
2) A circuit for connecting the current source to at least three electrodes on the scalp or cranium.
3) Where each electrode is connected at an instant to just one output of the current sources such that any instant each electrodes is an electrode sink or electrode source. The designation of electrode sink or electrode source defines the polarity of each electrode. Sink electrodes and source electrodes are said to have the opposite polarity.
4) Where the electrode positioning of the scalp and circuitry is such that, at any instant, all the electrodes of one polarity are circumscribed or surrounded by electrodes of another polarity.
5) (In a special case) where only one or two power sources (where a power source is considered one battery or several batteries in series and/or parallel) are used.
6) (In a special case) where additional functionality includes information from intelligent resistance measurement system.

In some implementation, it is considered desirable to reduce the number of current source to make the system robust, consume less power, be simpler to use of program, conform with standards, and/or other reasons. For example, it may be desired to use a single stimulator with just two outputs, a source and a sink. But using a single stimulator with just two outputs and connected each output to just one electrode, or to multiple electrodes in some ways, can, in some instances, result in unsafe and ineffective neurocranial stimulation. In some instances, therefore, it is helpful to apply a single stimulation source with two outputs.

In some implementations, it is desirable to consider the appropriate design of the stimulation source, such as voltage or current source or other, together with the nature of the connectivity to a plurality of electrodes, of which there are many permutations only a few of which typically are effective, and together with the positioning of the electrodes on the scalp, where again there are many permutations typically only a few that are suitable to provide very safe and effective neurocranial stimulation.

Some exemplary systems include:
1) at least five electrodes,
2) four electrodes share one polarity and circumscribe or surround an electrode of the opposite polarity,
3) where the current source is a DC current source for at least a portion of the stimulation exposure,
4) where additional circuit functionality includes a method to verify or validate that the electrode resistance of each of the four circumscribing electrodes is within a desired range.
5) where this desired range is at least substantially the same for each of the circumscribing electrodes. In one example the desired range is between 100 Ohm and 50 kOhm and in another example, it is between 1 kOhm and 10 kOhm,
6) (In a special case) where only two power sources (where a power source is considered one battery or several batteries in series and/or parallel) are used.

In another embodiment, electrodes of one polarity circumscribe or surround electrodes of the other polarity. The electrodes which are circumscribed or surrounded can, in some implementations, be a functional set. The electrodes, therefore, would have the features attributed to functional sets. Any number of electrodes can be circumscribed (e.g., one, two, three, four or more). In another embodiment, the electrodes that circumscribe or surround form a functional set or functional sets. In some embodiments, the number of electrodes that surround or circumscribe is two, three, four, five, six, or seven. In another embodiment, the number of electrodes that surround or circumscribe is equal to the number of electrodes that are surrounded or circumscribed plus two, three, four, five, six, seven, eight, nine, or ten. In another embodiment, the number of electrodes that surround or circumscribe is equal to the number of electrodes that are surrounded or circumscribed multiplied by two, three, four, five, or six.

In another embodiment, each functional set of the electrodes that surround or circumscribe is positioned on an opposite side of the electrodes that are surrounded of surrounded. In such a manner each functional set of the electrodes that surround or circumscribe may be assigned to a specific pie shape region emanating from the region of the electrodes that are surrounded of surrounded. Or the electrodes that form each functional set of the electrodes that surround or circumscribe may be positioned sufficiently close to each-other.

In another embodiment, a system includes:
1) At least one electrode on the scalp for electrical stimulation
2) A least one electrode on the scalp for electrical recording
3) An electrical circuit connected to at least one electrode for electrical stimulation and to at least one electrode for electrical recording
4) Where the circuit includes functionality for relating the output of at least one electrical stimulation electrode with an electrical signal generated near the recording electrode (where the electrical signal is generated as a result of stimulation).

5) (In a special case) where at least one stimulation electrode and one recording electrodes is on the scalp.

In a typical embodiment, the stimulation is maintained in the linear or near-linear range, or non-linearity is measured or predicted and incorporated into the said functionality for relating.

Systems and methods disclosed herein enable a user to validate proper placement of mechanical components, validate of system configuration, and moreover intermittently or continuously evaluate changes in component motion. This evaluation may be used to terminate stimulation, issue an alarm to the user or operator which allows them to make corrections, or may be integrated with an automatic stimulation control system such as Adaptive Electrical Stimulation functionality. By using appropriate and specific configurations, technologies, and algorithms, it is possible to use an electrode to detect the electrical potential (or voltage) generated on the surface of the body generated by the activity of another electrode (this measurement is evidently distinct from electrode impedance of EEG which is the electrical signal generated by the body). Using appropriate and specific configurations, technologies, and algorithms it is possible to use this information to validate the appropriate configuration of the stimulation system and the positioning of the electrodes. This can be done automatically or continuously prior to stimulation, during stimulation, or after stimulation.

In some embodiments, finite element methods are used to analyze the signal recorded at one or more electrodes. In another embodiment, techniques in linear algebra and matrix functions are use to analyze the signal recorded at two or more electrodes.

Typical currents applied are less than about 1 mA, and preferably less than 0.1 mA. The signals applied can be either DC or AC. If AC, the frequency used typically is greater than 100 Hz. In some embodiments, the frequency used is greater than 1 kHz.

In some implementations, the voltage generated on the scalp due to the current generated at a current source is linear over a certain range, meaning the peak voltage recorded scales linearly with the applied current and is independent of frequency. Firstly, this means that current sources should be used. Secondly, it means that the current can be decreased. It can be decreased to reduce skin sensation, to not interfere with the therapeutic stimulation, or for other reasons. Alternatively, one can use the same currents as used in therapy. Thirdly, how the body responds to electricity and how electricity is distorted by the electrode interface is very frequency dependent. Specifically, the body is less responsive to high frequency >100 Hz sinusoidal stimulation, and largely unresponsive to very high frequency >1 kHz sinusoidal stimulation. Specifically, the interference of the electrode-interface may be reduced by higher-frequencies. In addition, interference from the EEG or from motion is reduced by using high and very high frequencies, because EEG and motion may often have lower frequency content. The use of monitoring frequencies different from stimulation frequencies facilitates using the same electrode for stimulation and recording.

In some implementations, a system allows for monitoring and validation of system configuration using higher sinusoidal frequency currents.

In one example, a plurality of "exterior" electrode surrounds or circumscribes one "interior" electrode, or one interior electrode functional set. At any instant or during the course of stimulation, the exterior electrodes are all of one polarity and the surrounded/circumscribed electrode(s) is of the opposite polarity.

During transcranial electrical stimulation, current passage across the scalp generates voltage "artifacts" along the scalp. Using a recording electrode array, skin voltage artifacts resulting from transcranial electrical stimulation were mapped. Each of three stimulation electrode configurations tested resulted in a distinct distribution of scalp voltages; these spatial maps were linear with applied current amplitude (0 to 1 mA) and independent of frequency (0 to 100 Hz). Scalp voltage artifact recordings were used to validate an individualized high-resolution model of transcranial electrical stimulation. The model then correlated induced scalp voltage artifacts with predicted current flow through the cortex. Results show that high-resolution individualized FEM models accurately predict scalp voltages resulting from current flow across the scalp. Moreover, understanding current distribution though the scalp can guide the rational design of electrode configurations for brain modulation. Finally, monitoring of scalp voltage artifacts can be used to verify electrode placement to increase transcranial electrical stimulation and reproducibility.

Transcranial electrical stimulation encompasses a range of clinical and experimental protocols, including transcranial direct current stimulation (tDCS) and cranial electrotherapy stimulation (CES), which apply current through scalp electrodes for the purpose of modulating brain function. Applied current first distributes throughout the scalp, passes across the skull and CSF, eventually entering the brain.

Understanding the current distribution in the brain during transcranial electrical stimulation can help enhance safety in stimulation. Animal models, isolated skulls, and phantoms are of limited use in this regard because of the critical importance of anatomy and material properties. "Forward" models of transcranial electrical stimulation predict brain current flow (sphere models) and increasingly detailed "forward" models using finite element methods (FEM) have been developed. As FEM models may be used to characterize clinical electrotherapies as well as design new electrode montages it is important to experimentally validate the accuracy of these FEM models. Toward this end, though it is evidently not safe to record clinically with invasive intra-cortical electrodes, it is practical to record surface "artifact" potentials on the scalp that are generated during transcranial electrical stimulation.

During transcranial electrical stimulation, electrode configuration determines current distribution through the scalp, which is reflected in scalp voltage maps, and which ultimately determines the distribution of brain current flow. Scalp voltage artifacts were mapped and the accuracy of a subject-specific FEM model of transcranial electrical stimulation was validated. To precisely control the applied electrical stimulation, specialized high-density stimulation electrodes were used rather than large "sponge" electrodes. Three illustrative high-density stimulation montages were tested: 1) proximal-dipole; 2) distant-dipole; 3) and a 4×1 concentric-ring configuration (one electrode surrounded by four return electrodes). These montages resulted in distinct scalp surface artifacts that were precisely predicted by high-resolution FEM model. Moreover, these surface artifacts provide insight into the distribution of brain current flow and are thus useful to increase the efficacy and specificity of transcranial electrical stimulation. Furthermore, online artifact measurement can be used to increase the safety of transcranial electrical stimulation.

Imaging and Computational Methods:
MRI Acquisition and Segmentation
MRI of brain was performed on a 34 year old male with no neurological pathologies using a 3T Philips Achieva MRI scanner (Philips Medical Systems, Cleveland, Best, Netherlands). Three-dimensional spoiled gradient image (SPGR) was acquired with TE/TR=3 ms/6.6 ms, flip angle=8, acquisition matrix=256×256×190, voxel size=1×1×1 mm. Automatic segmentation was performed by FSL's Brain Extraction Tool (BET) and FSL's Automated Segmentation Toolbox (FAST). The head was segmented into four compartments: scalp, skull, cerebrospinal fluid (CSF), and brain. Further manual editing (Soterix, New York, N.Y.) was performed to correct the segmentation errors, and further segment the head into eight different tissue types: scalp, skull, CSF, brain tissue, eye, muscle, air, and marrow (Simpleware Ltd, Exeter, United Kingdom).

Stimulating Electrode Configurations

Following the 10-10 international system (conventionally used in EEG) 64 electrodes were automatically positioned on the segmented scalp surface using a customized MATLAB tool. All simulated electrodes were ~2 mm thick with a diameter of ~12 mm separated from the scalp by a 1-2 mm thick layer of gel. 2 or 5 electrodes were energized as stimulating electrodes according to one of following three electrode configurations; the remaining electrodes were not activated.

Three stimulation configurations were modeled and then tested experimentally

FEM Analysis

See Exemplary Methods.

Experimental Methods:

All experiments were approved by The City College of New York IRB. Experiments were performed on one 34 year old male, also used for individualized brain modeling. The subject was fitted with a conventional EEG cap with 64 electrode positions following the 10-10 international system; 2 or 5 positions were fitted with stimulation electrodes according to the three electrode configurations evaluated (as above), and the remaining positioned were used for recording.

Transcranial Electrical Stimulation

Transcranial electrical stimulation was applied using either an AM system analog isolated current source driven by a function generator or stand-alone Soterix 1×1 and 4×1 stimulators (Soterix, New York, N.Y.). Current was delivered using high-density stimulation electrodes and CCNY4 gel, where the stimulating electrodes replaced recording electrodes in the head-gear according to the stimulation configuration.

To minimize skin sensation and avoid irritation but maximize artifact S/N, ~0.4 mA peak current with a monophasic square wave or monophasic (offset) sine wave waveform was typically used for mapping measurements. But, as we validated the linearity of induced scalp potential with current amplitude (FIG. 32), all results are normalized to per-mA-of-current. Stimulation was applied in repeated exposures each less than 1 minute.

Surface Voltage Measurements

The surface voltage artifacts induced by transcranial electrical stimulation using methodology similar to EEG. We used two approaches to measure induced scalp potentials; the two technologies yielded identical results. In once case, scalp potential were measured sequentially between pairs of electrodes using a custom-made instrumentation amplifier. In the second case, scalp potentials were simultaneously measured from all scalp electrodes using the Bosomy EEG system. In both cases, scalp potential were measured using electrodes at multiple locations on the scalp following the 10-10 system—omitting the locations occupied by the stimulating electrodes (though the potential applied to the stimulating electrodes could be measured as the output of the current source, we suspected that because of the electrode interface voltage, this potential did not reflect the voltage at the scalp under the stimulation electrodes).

The main objective of this exemplary embodiment, was to characterize scalp potentials induced during transcranial electrical stimulation. In the process we validated the accuracy of FEM forward models of transcranial electrical stimulation by comparing predicted and measured induced scalp voltages. We evaluated distinct electrode montages to further consider implications for clinical electrode configuration design. As part of this analysis, we verified the temporal and spatial linearity of scalp voltages with applied current intensity and frequency.

Linearity of Scalp Voltage Artifacts with Stimulation Current Amplitude and Waveform In this exemplary embodiment, we first verified that scalp voltage artifact amplitude was a linear function of stimulation amplitude. Specifically, we show that the peak scalp voltage artifact measured between two electrodes on the scalp increases linearly with the peak applied current between two separate scalp stimulating electrodes; moreover in a frequency independent manner up to 100 Hz. Similarly, we show the profile of spatial maps is amplitude and frequency independent. This linearity allows us to normalize spatial maps to per-mA of applied current as well as to generalize our results to any stimulation intensity and waveform (e.g. AC, DC) within the linear range.

Spatial Maps of Scalp Voltage Artifacts During Transcranial Electrical Stimulation In this exemplary embodiment, we considered the scalp voltage artifact induced during transcranial electrical stimulation using three electrode montages. Results from experimental measurement were compared to a high-resolution FEM model (individualized to the same subject). Each electrode montage resulted in a distinct surface potential that was precisely predicted by the subject-specific FEM model. The FEM model also predicts the resulting cortical electric field for each electrode montage. In the discussion we consider the correlation between scalp current distributions (reflected in surface voltage artifacts) and predicted cortical electric fields (which relate to the induced neuro-modulation) in the design of targeted clinical electrotherapies.

When multiple current stimulators are used, the resulting brain electric fields reflect the independent contribution from each source. We verified this assumption at the level of the scalp. Specifically we show that stimulating with a 6 electrode configuration that combines the 4×1 configuration and the distant bipolar configuration (with the Cz location shared) results in a scalp voltages equal to the sum of scalp voltages generated independently by the 4×1 and distant-bipolar configurations. The combined 6-electrode experimental spatial map is also matched by FEM predictions. In the discussion we note the implications of temporal and spatial linearity for clinical dosage.

Non-linearity can arise from the electrode-tissue interface, which is mitigated by the use of current-controlled sources, or from changes in skin properties, which may occur near the stimulation electrode but were not significant enough to change overall scalp current distribution at the intensities we tested. Our results are consistent with linearity for weak low-frequency transcranial electrical stimulation.

Before applied current can effect brain function during transcranial electrical stimulation, current must pass through the scalp and other intermediate tissues. We recently proposed that dogma suggesting the skull is a "low-pass spatial filter" during transcranial current flow, diffusing current and severely limiting stimulation focality, was misguided. Rather, the high resistivity of the results leads to predominantly radial (undiffused) current flow—current diffusion, and modulation of focality, results other tissues namely the scalp and the CSF. The results of this study provide evidence for current diffusion at the level of the skin.

The degree and extent of current spread has direct implications for the design of electrode montages for effective transcranial current stimulation. Using bipolar montages, the spread of current across the scalp limited the focality of stimulation; use of smaller electrodes does not prevent this diffusion. The predicted focality of the 4×1 ring configuration results from the limit of current diffusion at the level of the scalp (Figure A9)—the size of the ring determines the extent of diffusion. Because current flow through the scalp is reflected in the induced scalp voltage artifacts, these artifacts may thus be generally considered in the design of targeted stimulation paradigms.

Because scalp voltage artifacts reflect the stimulation configuration (electrode montage, current intensity) they provide corroboration that a given clinical dose is being applied correctly. A fault in the device, a sudden problem with an electrode, or misplaced electrodes, will result in a deviation from an expected scalp voltage map (which is not necessarily evident in electrode resistance or stimulator output voltage); we suggest online monitoring scalp voltage artifacts may be incorporated as a safety feature in a stimulation device.

Any of the electrodes disclosed herein, in various implementations, can be an electrode, a DRIVER electrode, or a functional set. Where applicable, the connectivity indicated by a solid or dashed wire and/or by a numeric designation indicates a wire, circuit, booster, or buffer, or monitor (which may be configured with regulator). Whether or not indicated, when multiple configurations are shown they may be equivalent electrode configurations. Whether or not indicated, adaptive equivalent stimulation may be applied to any configuration. It will be understood that as described in this invention a single device may implement two more of any of the configurations/circuits/systems shown or permutations of these configurations/circuits/systems.

The order that steps discussed in connection with various methods can be modified. Indeed, in some implementations, entire steps or sequences of steps may be omitted.

References to a patient's head can, in some implementations, include the neck and/or others areas near or around head. In some cases, in addition to at least one cranial electrode, one or more extra-cephalic electrodes may be used including an electrode placed on the arm.

Any number of components (e.g., electrodes, current sources, etc. and can be connected to one another in a wide variety of manners. Indeed, in some implementations, redundant current sources, electrodes, or other system components can be introduced.

Current sources can have more than two terminals (e.g., in some implementations, a current source can include one or more three pole devices). In such cases it would be understood that multi-pole devices may be represented as two or more dipole devices and applied as outline in this invention.

The term patient, as used herein, refers generally to any person to whom the electrodes are, are to be or were connected to for neurocranial stimulation or other therapeutic purposes.

The devices, systems and techniques disclosed herein can be used to treat neurological disorders. "The term "neurological disorder" or "neurological disorders", as used herein, refers to any disorder, disease, and/or syndrome due to or resulting from neurologic, psychiatric, psychological, and/or cerebrovascular symptomology or origin. The term "neurological disorder" or "neurological disorders", as used herein, also refers to diseases, disorder or condition of the brain and nervous system or psychiatric disorders or conditions. Neurological disorders include, but are not limited to Absence of the Septum Pellucidum, Acquired Epileptiform Aphasia, Acute Disseminated Encephalomyelitis, ADHD, Adie's Pupil, Adie's Syndrome, Adreno leukodystrophy, Agenesis of the Corpus Callosum, Agnosia, Aicardi Syndrome, AIDS—Neurological Complications, Alexander Disease, Alpers' Disease, Alternating Hemiplegia, Alzheimer's Disease, Amyotrophic Lateral Sclerosis, Anencephaly, Aneurysm, Angelman Syndrome, Angiomatosis, Anoxia, Aphasia, Apraxia, Arachnoid Cysts, Arachnoiditis, Arnold-Chiari Malformation, Arteriovenous Malformation, Asperger Syndrome, Ataxia, Ataxia, Telangiectasia, Ataxias and Cerebellar/Spinocerebellar Degeneration, Attention Deficit-Hyperactivity Disorder, Autism, Autonomic Dysfunction, Back Pain, Barth Syndrome Batten Disease, Becker's Myotonia, Behcet's Disease, Bell's Palsy, Benign Essential Blepharospasm, Benign Focal Amyotrophy, Benign Intracranial Hypertension, Bernhardt-Roth Syndrome, Binswanger's Disease, Blepharospasm, Bloch-Sulzberger Syndrome, Brachial Plexus Birth Injuries, Brachial Plexus Injuries, Bradbury-Eggleston Syndrome, Brain and Spinal Tumors, Brain Aneurysm, Brain Injury, Brown-Sequard Syndrome, Bulbospinal Muscular Atrophy, Canavan Disease, Carpal Tunnel Syndrome Causalgia, Cavernomas, Cavernous Angioma, Cavernous Malformation, Central Cervical Cord Syndrome, Central Cord Syndrome, Central Pain Syndrome, Cephalic Disorders, Cerebellar Degeneration, Cerebellar Hypoplasia, Cerebral Aneurysm, Cerebral Arteriosclerosis, Cerebral Atrophy, Cerebral Beriberi, Cerebral Gigantism, Cerebral Hypoxia, Cerebral Palsy, Cerebro-Oculo-Facio-Skeletal Syndrome, Charcot-Marie-Tooth Disease, Chiari Malformation, Chorea, Choreoacanthocytosis, Chronic Inflammatory Demyelinating Polyneuropathy (CIDP), Chronic Orthostatic Intolerance, Chronic Pain Cockayne Syndrome Type II, Coffin Lowry Syndrome, COFS, Colpocephaly, Coma and Persistent Vegetative State, Complex Regional Pain Syndrome, Congenital Facial Diplegia, Congenital Myasthenia, Congenital Myopathy, Congenital Vascular Cavernous, Malformations, Corticobasal Degeneration, Cranial Arteritis, Craniosynostosis, Creutzfeldt—Jakob Disease, Cumulative Trauma Disorders, Cushing's Syndrome, Cytomegalic Inclusion Body Disease, Cytomegalovirus Infection, Dancing Eyes-Dancing Feet Syndrome, Dandy-Walker Syndrome, Dawson Disease, De Morsier's Syndrome, Deep Brain Stimulation for Parkinson's Disease, Dejerine-Klumpke Palsy, Dementia, Dementia—Multi-Infarct, Dementia—Semantic, Dementia—Subcortical, Dementia With Lewy Bodies, Dentate Cerebellar Ataxia, Dentatorubral Atrophy, Dermatomyositis, Developmental Dyspraxia, Devic's Syndrome, Diabetic Neuropathy, Diffuse Sclerosis, Dysautonomia, Dysgraphia, Dyslexia, Dysphagia, Dyspraxia, Dyssynergia Cerebellaris, Myoclonica, Dyssynergia Cerebellaris Progressiva, Dystonias, Early Infantile Epileptic, Encephalopathy, Empty Sella Syndrome, Encephalitis Lethargica, Encephaloceles, Encephalopathy, Encephalotrigeminal Angiomatosis, Epilepsy, Erb-Duchenne and Dejerine-Klumpke Palsies, Erb's Palsy, Fabry's Disease, Fahr's Syndrome, Fainting, Familial Dysautonomia, Familial Hemangioma, Familial Idiopathic Basal Ganglia, Calcification, Familial Periodic Paralyses, Familial Spastic Paralysis, Febrile Seizures, Fisher Syndrome, Floppy Infant Syndrome, Friedreich's Ataxia, Frontotemporal, Dementia, Gaucher's Disease, Gerstmann's Syndrome, Gerstmann-Straussler-Scheinker, Disease, Giant Cell Arteritis, Giant Cell Inclusion Disease, Globoid Cell Leukodystrophy, Glossopharyngeal Neuralgia, Guillain-Barre Syndrome, Hallervorden-Spatz Disease, Head Injury, Headache, Hemicrania Continua, Hemifacial Spasm, Hemiplegia Alterans, Hereditary Neuropathies, Hereditary Spastic Paraplegia, Heredopathia Atactica, Polyneuritiformis, Herpes Zoster, Herpes Zoster Oticus, Hirayama Syndrome, Holmes-Adie syndrome, Holoprosencephaly, HTLV-I Associated, Myelopathy, Huntington's Disease, Hydranencephaly, Hydrocephalus, Hydrocephalus—Normal Pressure, Hydromyeiia, Hyperactivity, Hypercortisolism, Hypersomnia, Hypertonia, Hypotonia, —Infantile, Hypoxia, Immune-Mediated Encephalomyelitis, Inclusion Body Myositis, Incontinentia Pigmenti, Infantile Hypotonia, Infantile Neuroaxonal Dystrophy, Infantile Phytanic Acid Storage Disease, Infantile Refsum Disease, Infantile Spasms, Inflammatory Myopathy, Iniencephaly, Intestinal Lipodystrophy, Intracranial Cysts, Intracranial Hypertension, Isaac's Syndrome, Joubert Syndrome, Kearns-Sayre Syndrome, Kennedy's Disease, Kinsbourne syndrome, Kleine-Levin Syndrome, Klippel-Feil Syndrome, Klippel-Trenaunay Syndrome (KTS), Klüver-Bucy Syndrome, Korsakoffs Amnesic Syndrome, Krabbe Disease, Kugelberg-Welander Disease, Kuru, Lambert-Eaton Myasthenic Syndrome, Landau-Kleffner Syndrome, Lateral Femoral, Cutaneous Nerve Entrapment, Lateral Medullary Syndrome, Learning Disabilities, Leigh's Disease, Lennox-Gastaut Syndrome, Lesch-Nyhan Syndrome, Leukodystrophy, Levine-Critchley Syndrome, Lewy Body Dementia, Lipid Storage Diseases, Lissencephaly, Locked-In Syndrome, Lou Gehrig's Disease, Lupus—Neurological, Sequelae, Lyme Disease—Neurological Complications, Machado-Joseph Disease, Macrencephaly, Mania, Megalencephaly, Melkersson-Rosenthal Syndrome, Meningitis, Meningitis and Encephalitis, Menkes Disease, Meralgia Paresthetica, Metachromatic, Leukodystrophy, Microcephaly, Migraine, Miller Fisher Syndrome, Mini-Strokes, Mitochondrial Myopathies, Mobius Syndrome, Monomelic Amyotrophy, Motor Neuron Diseases, Moyamoya Disease, Mucolipidoses, Mucopolysaccharidoses, Multifocal Motor Neuropathy, Multi-Infarct Dementia, Multiple Sclerosis, Multiple System Atrophy, Multiple System Atrophy with Orthostatic Hypotension, Muscular Dystrophy, Myasthenia—Congenital, Myasthenia Gravis, Myelinoclastic Diffuse Sclerosis, Myoclonic Encephalopathy of Infants, Myoclonus, Myopathy, Myopathy—Congenital, Myopathy—Thyrotoxic, Myotonia, Myotonia Congenita, Narcolepsy, Neuroacanthocytosis, Neurodegeneration with Brain Iron Accumulation, Neurofibromatosis, Neuroleptic Malignant Syndrome, Neurological Complications of AIDS, Neurological Complications Of Lyme Disease, Neurological Consequences of Cytomegalovirus Infection, Neurological Manifestations of Pompe Disease, Neurological Sequelae Of Lupus, Neuromyelitis Optica, Neuromyotonia, Neuronal Ceroid, Lipofuscinosis, Neuronal Migration Disorders, Neuropathy—Hereditary, Neurosarcoidosis, Neurotoxicity, Nevus Cavernosus, Niemann-Pick Disease, Normal Pressure Hydrocephalus, Occipital Neuralgia, Obesity, Occult Spinal Dysraphism Sequence, Ohtahara Syndrome, Olivopontocerebellar Atrophy, Opsoclonus Myoclonus, Orthostatic Hypotension, O'Sullivan-McLeod Syndrome, Overuse Syndrome, Pain—Chronic, Paine, Pantothenate Kinase-Associated Neurodegeneration, Paraneoplastic Syndromes, Paresthesia, Parkinson's Disease, Paroxysmal Choreoathetosis, Paroxysmal Hemicrania, Parry-Romberg, Pelizaeus-Merzbacher Disease, Pena Shokeir II Syndrome, Perineural Cysts, Periodic Paralyses, Peripheral Neuropathy, Periventricular Leukomalacia, Persistent Vegetative State, Pervasive Developmental Disorders, Phytanic Acid Storage Disease, Pick's Disease, Pinched Nerve, Piriformis Syndrome, Pituitary Tumors, Polymyositis, Pompe Disease, Porencephaly, Postherpetic Neuralgia, Postinfectious Encephalomyelitis, Post-Polio Syndrome, Postural Hypotension, Postural Orthostatic, Tachycardia Syndrome, Postural Tachycardia Syndrome, Primary Dentatum Atrophy, Primary Lateral Sclerosis, Primary Progressive Aphasia, Prion Diseases, Progressive Hemifacial Atrophy, Progressive Locomotor Ataxia, Progressive Multifocal, Leukoencephalopathy, Progressive Sclerosing Poliodystrophy, Progressive Supranuclear, Palsy, Prosopagnosia, Pseudotumor Cerebri, Ramsay Hunt Syndrome I (formerly known as), Ramsay Hunt Syndrome II (formerly known as), Rasmussen's Encephalitis, Reflex Sympathetic Dystrophy Syndrome, Refsum Disease, Refsum Disease—Infantile, Repetitive Motion Disorders, Repetitive Stress Injuries, Restless Legs Syndrome, Retrovirus-Associated, Myelopathy, Rett Syndrome, Reye's Syndrome, Riley-Day Syndrome, Sacral Nerve Root Cysts, Saint Vitus Dance, Salivary Gland Disease, Sandhoff Disease, Schilder's Disease, Schizencephaly, Seitelberger Disease, Seizure Disorder, Semantic Dementia, Septo-Optic Dysplasia, Shaken Baby Syndrome, Shingles Shy-Drager Syndrome, Sjogren's Syndrome, Sleep Apnea, Sleeping Sickness, Sotos Syndrome, Spasticity, Spina Bifida, Spinal Cord Infarction, Spinal Cord Injury, Spinal Cord Tumors, Spinal Muscular Atrophy, Spinocerebellar Atrophy, Spinocerebellar, Degeneration, Steele-Richardson-Oiszewski Syndrome, Stiff-Person Syndrome, Striatonigral Degeneration, Stroke, Sturge-Weber Syndrome, Subacute Sclerosing Panencephalitis, Subcortical Arteriosclerotic Encephalopathy, SUNCT Headache Swallowing Disorders, Sydenham Chorea, Syncope, Syphilitic Spinal Sclerosis, Syringohydromyelia, Syringomyelia, Systemic Lupus Erythematosus, Tabes Dorsalis Tardive Dyskinesia, Tarlov Cysts, Tay-Sachs Disease, Temporal Arteritis, Tethered Spinal Cord Syndrome, Thomsen's Myotonia, Thoracic Outlet Syndrome, Thyrotoxic Myopathy, Tic Douloureux, Todd's Paralysis, Tourette Syndrome, Transient Ischemic Attack, Transmissible Spongiform Encephalopathies, Transverse Myelitis, Traumatic Brain Injury, Tremor, Trigeminal Neuralgia, Tropical Spastic Paraparesis, Tuberous Sclerosis, Vascular Erectile Tumor, Vasculitis including Temporal Arteritis, Von Economo's Disease, Von Hippel-Lindau Disease (VHL), Von Recklinghausen's Disease, Wallenberg's Syndrome, Werdnig-Hoffman Disease, Wernicke-Korsakoff Syndrome, West Syndrome, Whiplash, Whipple's Disease, Williams Syndrome, Wilson's Disease, X-Linked Spinal and Bulbar Muscular Atrophy, or Zellweger Syndrome.

Other technologies where the invention described here can be directly applied include deep brain stimulation, cortical electrical stimulation, vagus nerve stimulation, spinal chord stimulation, cardiac stimulation, pace-maker stimulation, defibrillator stimulation, cochlear implants, cerebellum stimulation, motor cortex stimulation, muscle stimulation, electrical epilepsy control, stimulation with implanted electrodes, and especially those application of the above where three or more electrodes are energized and especially those applications where there is a desire to regulate the current at the energized electrodes.

Other implementations are within the scope of the following claims.

What is claimed is:
1. A method comprising:
coupling a plurality of electrodes to a patient's head;
identifying whether two or more of the electrodes form a functional set, such that a desired therapeutic effect can be achieved when the two or more electrodes deliver a total amount of current to the patient regardless of what portion of the total amount of current each respective electrode in the functional set delivers;

providing one or more constant current sources, each having a supply terminal and a return terminal, wherein the current supplied at the supply terminal is equal to current returned to the return terminal;

coupling the one or more constant current sources to the electrodes such that each supply terminal and each return terminal is coupled to no more than the electrodes of a single one of the functional sets, if any, or to a single one of the electrodes not included in one of the functional set;

monitoring a voltage being produced across the constant current source's supply and return terminals to provide at least an indirect measure of resistance; and in response to one of the monitored voltages exceeding a threshold value:
reducing an amount of current passing through a corresponding one of the electrodes; and
increasing an amount of current being delivered at a different one or more of the electrodes by an amount approximately equal to the amount of current that is reduced.

2. The method of claim 1, wherein a rate of change associated with reducing or increasing the amounts of current flowing does not exceed approximately 1 milliamp per second.

3. The method of claim 1, further comprising:
coupling more than one of the supply terminals or more than one of the return terminals to the electrodes of a single one of the functional sets, if any, or to a single one of the electrodes, if any, not included in the functional sets.

4. The method of claim 1, further comprising:
delivering a substantially constant amount of current to each respective functional set, if any; and
delivering a substantially constant amount of current to each respective electrode, if any, not included in one of the functional sets.

5. The method of claim 4 further comprising:
limiting a rate of change associated with the current being delivered to each electrode to no more than approximately 1 milliamp per second.

6. The method of claim 1, wherein the plurality of electrodes includes at least one functional set.

7. The method of claim 1, wherein the plurality of electrodes includes at least one electrode not included in one of the functional sets.

8. The method of claim 1, wherein identifying the one or more functional sets comprises considering one or more of the following factors:
physical proximity of same polarity electrodes to one another;
electrical resistance between adjacent same polarity electrodes; and
physical arrangement of electrodes having a first polarity relative to electrodes of a second polarity.

9. The method of claim 8 wherein a functional set can include one or more of the following:
a pair of same polarity electrodes that are within about 4 centimeters, more preferably less than about 2 centimeter of one another and more preferably touching one another;
a pair of same polarity electrodes that have a resistance between them of less than about 1 kOhm, less than about 200 ohms, less than about 100 Ohms, less than about 10 Ohms, less than about 1 Ohm or close to zero ohms; and
a same polarity electrode or plurality of same polarity electrodes surrounded by three or more electrodes having an opposite polarity.

10. The method of claim 1, wherein two or more electrodes that are physically in contact with one another form a functional set.

11. The method of claim 1, wherein identifying whether two or more of the electrodes form a functional set comprises:
measuring or estimating a resistance from one electrode to another electrode of the same polarity.

12. The method of claim 1, wherein identifying whether two or more of the electrodes form a functional set comprises identifying one or more electrodes of a first polarity substantially surrounded by four electrodes of a second polarity different than the first.

13. The method of claim 1, wherein each electrode can be included in no more than one of the functional sets.

14. The method of claim 1, wherein the one or more electrodes that experience an increase in the amount of current flowing are in a functional set with the electrode that experiences a reduction in the amount of current flowing.

15. The method of claim 1, wherein the desired therapeutic effect can be achieved as long as the electric field strength produced by the current flow at any location within the target tissue is not changed by more than approximately 50%, or wherein a peak electric field in the brain is not changed by more than 15%, or wherein an area of cortical surface that is greater than 50%, 75%, or 90% or the peak cortical field does not change more than 10 cm2, or wherein an average electric field in the target tissue does not change by more than approximately 50% OR any combination of the foregoing.

16. The method of claim 1, wherein the two or more electrodes forming the functional set are substantially surrounded by a group of outer peripheral electrodes of the opposite polarity.

17. The method of claim 1, further comprising:
substantially changing the distribution of the total current across the electrodes of the functional set.

18. A method comprising:
coupling a plurality of electrodes to a patient's head;
identifying whether two or more of the electrodes form a functional set, such that a desired therapeutic effect can be achieved when the two or more electrodes deliver a total amount of current to the patient regardless of what portion of the total amount of current each respective electrode in the functional set delivers;
providing one or more constant current sources, each having a supply terminal and a return terminal, wherein the current supplied at the supply terminal is equal to current returned to the return terminal; and
coupling the one or more constant current sources to the electrodes such that each supply terminal and each return terminal is coupled to no more than the electrodes of a single one of the functional sets, if any, or to a single one of the electrodes not included in one of the functional set,
wherein the one or more constant current sources are alternating current sources and wherein at any particular time during operation, each terminal of the one or more constant current sources is acting as either a supply terminal or a return terminal.

19. The method of claim 18, further comprising:
monitoring an electrical resistance between the supply terminal and return terminal for one or more of the constant current sources while current is being delivered by the one or more constant current sources to the patient.

20. The method of claim 18, further comprising:
monitoring a voltage being produced across the constant current source's supply and return terminals to provide at least an indirect measure of resistance.

21. A method comprising:
coupling a plurality of electrodes to a patient's head;
identifying whether two or more of the electrodes form a functional set, such that a desired therapeutic effect can be achieved when the two or more electrodes deliver a total amount of current to the patient regardless of what portion of the total amount of current each respective electrode in the functional set delivers, wherein identifying whether two or more of the electrodes form a functional set comprises identifying one or more electrodes of a first polarity substantially surrounded by four electrodes of a second polarity different than the first;
providing one or more constant current sources, each having a supply terminal and a return terminal, wherein the current supplied at the supply terminal is equal to current returned to the return terminal;
coupling the one or more constant current sources to the electrodes such that each supply terminal and each return terminal is coupled to no more than the electrodes of a single one of the functional sets, if any, or to a single one of the electrodes not included in one of the functional set;
delivering current to the patient's body from the supply terminals of four constant current sources through the one or more electrodes of the first polarity; and
returning current from the patient's body to the return terminals of the four constant current sources through the four electrodes of the second polarity.

22. A method comprising:
coupling a plurality of electrodes to a patient's head;
identifying whether two or more of the electrodes form a functional set, such that a desired therapeutic effect can be achieved when the two or more electrodes deliver a total amount of current to the patient regardless of what portion of the total amount of current each respective electrode in the functional set delivers, wherein identifying whether two or more of the electrodes form a functional set comprises identifying one or more electrodes of a first polarity substantially surrounded by four electrodes of a second polarity different than the first;
providing one or more constant current sources, each having a supply terminal and a return terminal, wherein the current supplied at the supply terminal is equal to current returned to the return terminal;
coupling the one or more constant current sources to the electrodes such that each supply terminal and each return terminal is coupled to no more than the electrodes of a single one of the functional sets, if any, or to a single one of the electrodes not included in one of the functional set;
delivering current to the patient's body from the supply terminals of four constant current sources through the four electrodes of the second polarity, respectively; and
returning current from the patient's body to the return terminals of the four constant current sources through the one or more electrodes of the first polarity.

23. A method comprising:
coupling a plurality of electrodes to a patient's head;
identifying whether two or more of the electrodes form a functional set, such that a desired therapeutic effect can be achieved when the two or more electrodes deliver a total amount of current to the patient regardless of what portion of the total amount of current each respective electrode in the functional set delivers, wherein identifying whether two or more of the electrodes form a functional set comprises identifying one or more electrodes of a first polarity substantially surrounded by four electrodes of a second polarity different than the first;
providing one or more constant current sources, each having a supply terminal and a return terminal, wherein the current supplied at the supply terminal is equal to current returned to the return terminal;
coupling the one or more constant current sources to the electrodes such that each supply terminal and each return terminal is coupled to no more than the electrodes of a single one of the functional sets, if any, or to a single one of the electrodes not included in one of the functional set;
delivering current to the patient's body from the supply electrode of a single one of the constant current sources through the one or more electrodes of the first polarity; and
returning current from the patient's body to the return terminal of the single one of the constant current sources through the four electrodes of the second polarity.

24. A method comprising:
coupling a plurality of electrodes to a patient's head;
identifying whether two or more of the electrodes form a functional set, such that a desired therapeutic effect can be achieved when the two or more electrodes deliver a total amount of current to the patient regardless of what portion of the total amount of current each respective electrode in the functional set delivers, wherein identifying whether two or more of the electrodes form a functional set comprises identifying one or more electrodes of a first polarity substantially surrounded by four electrodes of a second polarity different than the first;
providing one or more constant current sources, each having a supply terminal and a return terminal, wherein the current supplied at the supply terminal is equal to current returned to the return terminal;
coupling the one or more constant current sources to the electrodes such that each supply terminal and each return terminal is coupled to no more than the electrodes of a single one of the functional sets, if any, or to a single one of the electrodes not included in one of the functional set;
delivering current to the patient's body from the supply terminal of a single one of the constant current sources through the four electrodes of the second polarity; and
returning current from the patient's body to the return terminal of the single one of the constant current sources through the one or more electrodes of the first polarity.

\* \* \* \* \*